United States Patent
Vogelbaum et al.

(10) Patent No.: US 8,808,234 B2
(45) Date of Patent: Aug. 19, 2014

(54) CATHETER ASSEMBLY

(75) Inventors: Michael A. Vogelbaum, Moreland Hills, OH (US); Ji-Feng Chen, Lakewood, OH (US); Shengqiang Gao, Beachwood, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 751 days.

(21) Appl. No.: 13/044,963

(22) Filed: Mar. 10, 2011

(65) Prior Publication Data

US 2011/0224607 A1    Sep. 15, 2011

Related U.S. Application Data

(60) Provisional application No. 61/312,401, filed on Mar. 10, 2010.

(51) Int. Cl.
*A61M 29/00* (2006.01)
*A61M 25/00* (2006.01)
*A61M 25/01* (2006.01)
*A61M 25/10* (2013.01)

(52) U.S. Cl.
CPC ....... *A61M 25/10* (2013.01); *A61M 2025/1086* (2013.01); *A61M 25/0074* (2013.01); *A61M 2025/1081* (2013.01); *A61M 2025/004* (2013.01); *A61M 25/0082* (2013.01); *A61M 25/0068* (2013.01); *A61M 2025/0096* (2013.01); *A61M 25/0097* (2013.01); *A61M 2025/0057* (2013.01); *A61M 2025/0042* (2013.01); *A61M 2025/105* (2013.01); *A61M 2025/0024* (2013.01); *A61M 25/0102* (2013.01)
USPC ..................................... 604/96.01

(58) Field of Classification Search
CPC ............ A61M 25/0631; A61M 25/04; A61M 25/0662; A61M 2025/0042; A61M 2025/0057
USPC ................................ 604/95.04, 96.01, 164.01
See application file for complete search history.

(56) References Cited

U.S. PATENT DOCUMENTS

| | | | |
|---|---|---|---|
| 5,112,305 A | 5/1992 | Barath et al. | |
| 5,217,474 A | 6/1993 | Zacca et al. | |
| 5,344,439 A * | 9/1994 | Otten ........................... | 607/126 |
| 5,354,279 A | 10/1994 | Hofling | |
| 5,419,777 A * | 5/1995 | Hofling ......................... | 604/264 |
| 5,441,481 A | 8/1995 | Mishra et al. | |
| 5,454,790 A | 10/1995 | Dubrul | |

(Continued)

FOREIGN PATENT DOCUMENTS

WO    WO-2008/020967 A2    2/2008
WO    WO-2008/115566 A2    9/2008

OTHER PUBLICATIONS

An International Search Report dated Nov. 25, 2011 for PCT International Application No. PCT/US2011/027879, filed Mar. 10, 2011.

*Primary Examiner* — Nicholas Lucchesi
*Assistant Examiner* — Diva K Chander
(74) *Attorney, Agent, or Firm* — Tarolli, Sundheim, Covell & Tummino LLP

(57) ABSTRACT

A catheter assembly comprises a first catheter including a wall with an inner surface at least partially defining a lumen. A second catheter is connected to the wall of the first catheter and is disposed outward of the inner surface of the wall. The second catheter is at least partially covered by a sheath portion of the first catheter.

44 Claims, 9 Drawing Sheets

(56) References Cited

U.S. PATENT DOCUMENTS

| | | |
|---|---|---|
| 5,464,395 A | 11/1995 | Faxon et al. |
| 5,588,960 A | 12/1996 | Edwards et al. |
| 5,693,029 A | 12/1997 | Leonhardt |
| 6,102,904 A | 8/2000 | Vigil et al. |
| 6,302,870 B1 * | 10/2001 | Jacobsen et al. ............... 604/272 |
| 6,458,098 B1 | 10/2002 | Kanesaka |
| 6,537,241 B1 | 3/2003 | Odland |
| 7,566,316 B2 * | 7/2009 | McGuckin et al. .......... 604/6.16 |
| 7,691,086 B2 * | 4/2010 | Tkebuchava ............. 604/164.01 |
| 7,883,492 B2 | 2/2011 | Mittermeyer et al. |
| 7,959,595 B2 * | 6/2011 | Melsheimer et al. ........ 604/6.16 |
| 8,298,187 B2 * | 10/2012 | Woodard et al. ......... 604/164.12 |
| 2003/0167031 A1 | 9/2003 | Odland |
| 2006/0116636 A1 | 6/2006 | Murphy et al. |
| 2006/0129178 A1 | 6/2006 | Reifart et al. |
| 2008/0294096 A1 | 11/2008 | Uber, III et al. |
| 2009/0082758 A1 | 3/2009 | Gill et al. |

* cited by examiner

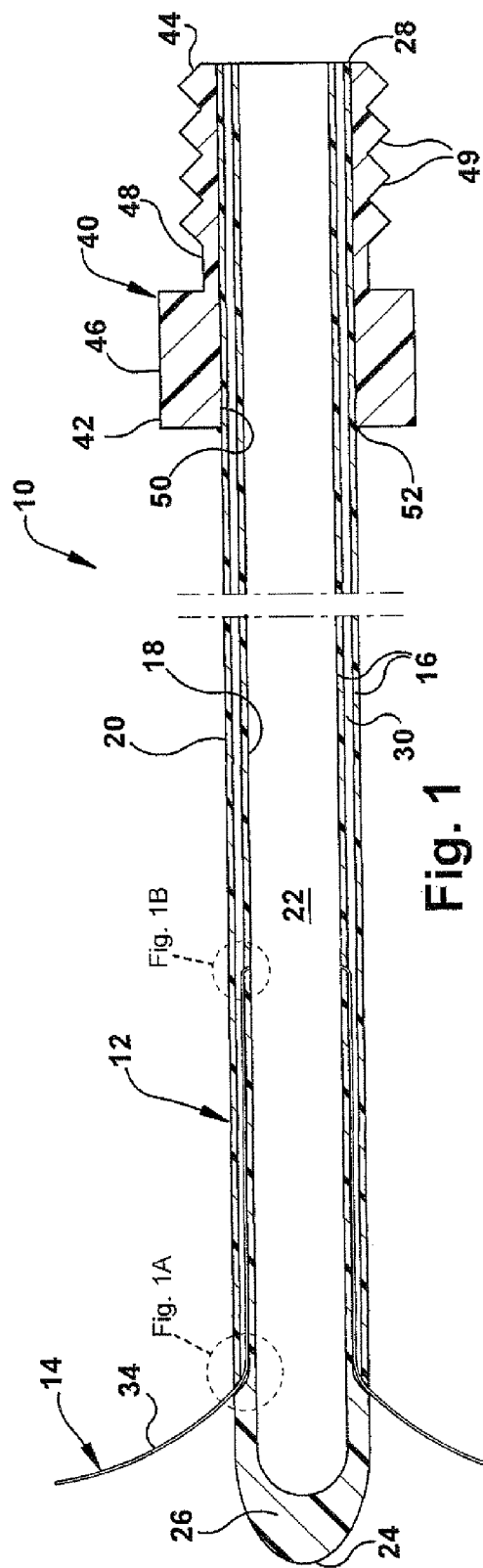
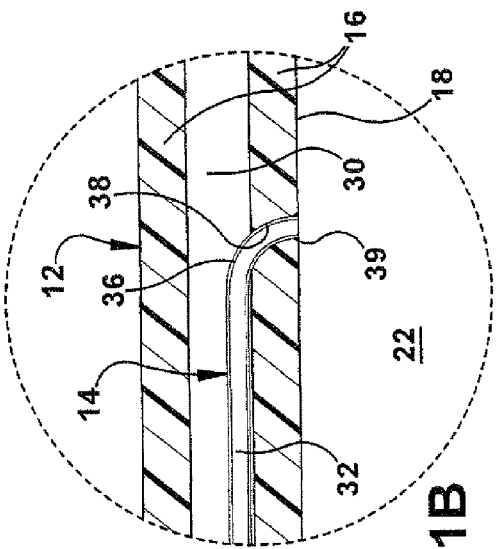
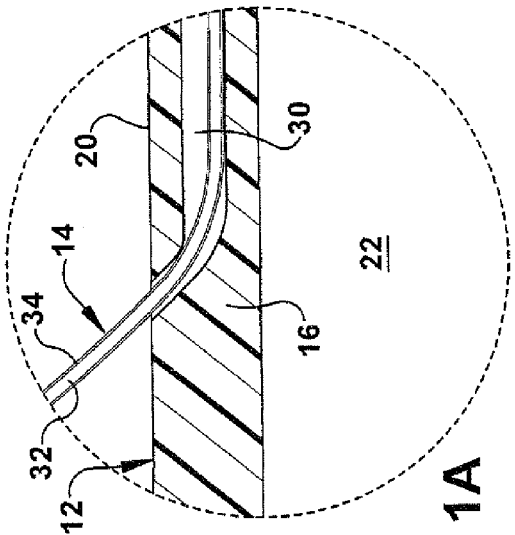

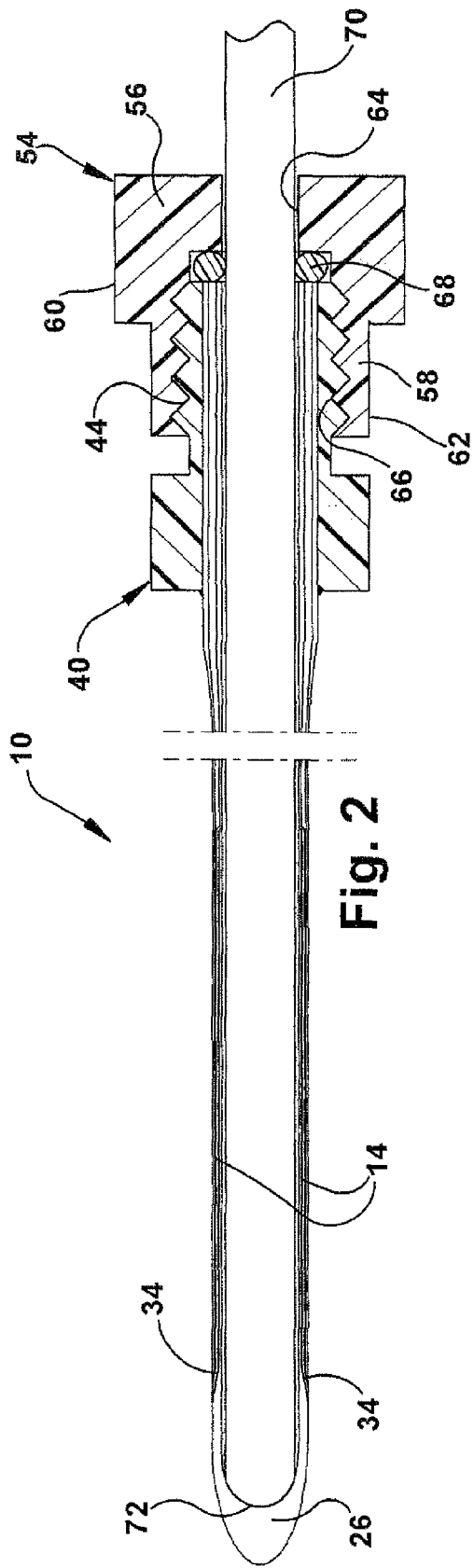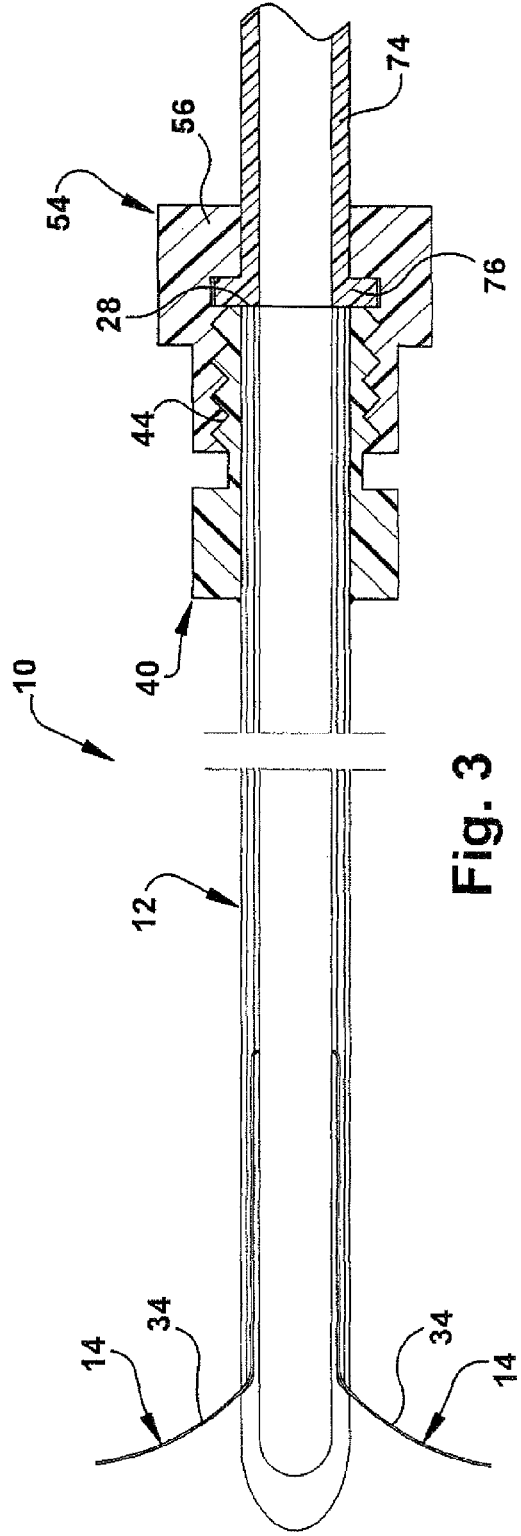

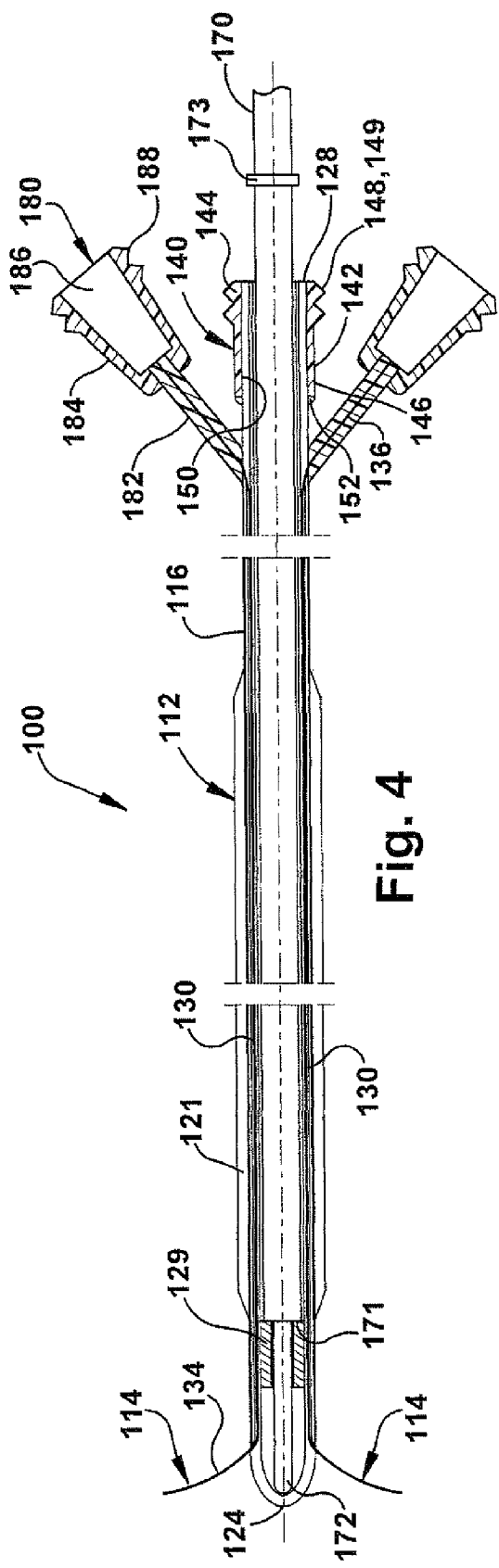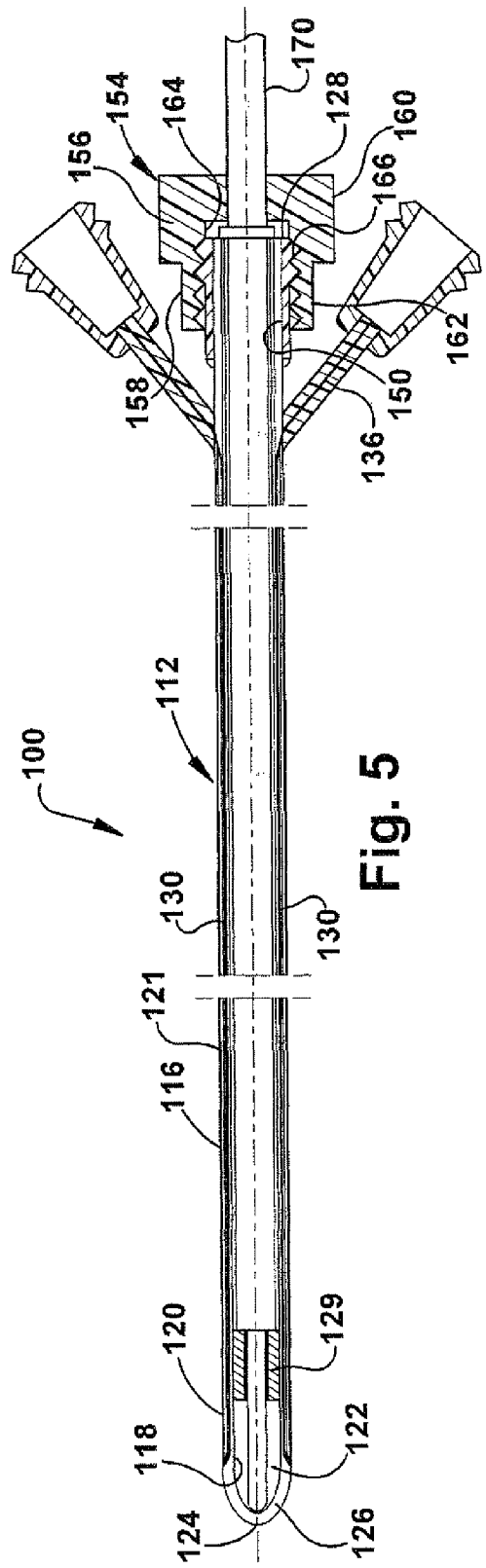

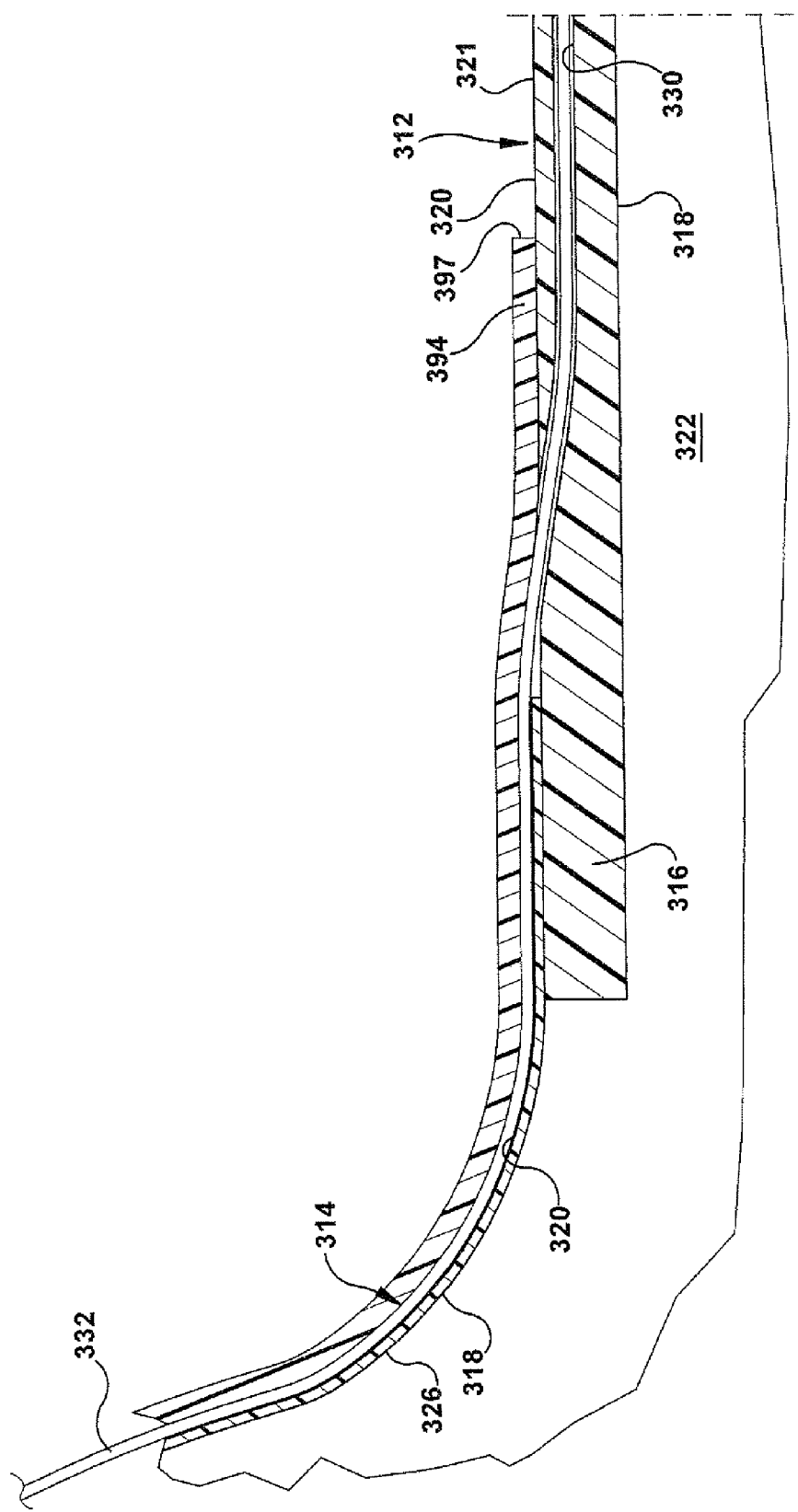

US 8,808,234 B2

CATHETER ASSEMBLY

RELATED APPLICATION

This application claims priority from U.S. Provisional Application Ser. No. 61/312,401, filed Mar. 10, 2010, the subject matter, which is incorporated herein by reference in its entirety.

FIELD OF THE INVENTION

The present invention relates to a catheter assembly that comprises two connected catheters and, more particularly, to a catheter assembly in which one catheter is at least partially covered by a sheath portion of another catheter.

BACKGROUND OF THE INVENTION

Convection enhanced delivery ("CED") of a bioactive agent involves introducing a fluid containing the bioactive agent into a patient's tissue under pressure so that the fluid moves through the tissue via bulk flow. Implementing CED generally involves inserting multiple catheters into the tissue to be treated, such as cerebral tissue. To reduce the risk of hemorrhage and/or trauma to the tissue, it is desirable for the catheters to be microcatheters with small outside diameters.

SUMMARY OF THE INVENTION

The present invention is directed to a catheter assembly that comprises two connected catheters and, more particularly, to a catheter assembly in which one catheter is at least partially covered by a sheath portion of another catheter.

In accordance with an embodiment of the present invention, a catheter assembly comprises a first catheter including a wall with an inner surface at least partially defining a lumen. A second catheter is connected to the wall of the first catheter and is disposed outward of the inner surface of the wall. The second catheter is at least partially covered by a sheath portion of the first catheter.

In accordance with another embodiment of the present invention, a catheter assembly comprises a first catheter including a wall with an inner surface at least partially defining a lumen. A second catheter is disposed outward of the inner surface of the wall of the first catheter. The second catheter is at least partially fixed to the wall of the first catheter.

In accordance with still another embodiment of the invention, a catheter assembly comprises a first catheter including a wall with an inner surface at least partially defining a lumen extending lengthwise of the first catheter. A second catheter is at least partially disposed in the wall of the first catheter outward of the inner surface of the wall and extending lengthwise of the first catheter.

In accordance with a further embodiment of the invention, a catheter assembly comprises a first catheter including a wall at least partially defining a lumen. A lengthwise portion of the wall is made of a resilient material and is longitudinally extensible. The lengthwise portion of the wall has a diameter that is reduced when the lengthwise portion of the wall is longitudinally extended. The diameter of the lengthwise portion of the wall increases from a reduced condition when the lengthwise portion of the wall resiliently returns from a longitudinally extended condition.

In accordance with yet a further embodiment of the invention, a catheter assembly comprises a first catheter including a wall with an inner surface at least partially defining a lumen. A second catheter is disposed outward of the inner surface of the wall. At least a portion of the wall of the first catheter is made of a resilient material and is extensible. The second catheter is connected to the portion of the wall of the first catheter. Extension of the portion of the wall causes a portion of the second catheter to be pulled from a first position to a second position.

In accordance with still a further embodiment of the invention, a catheter assembly comprises (a) a catheter including a lumen and (b) a piece of material connected to the catheter. Movement of the piece of material pulls at least a portion of the catheter from a first position to a second position.

BRIEF DESCRIPTION OF THE DRAWINGS

The foregoing and other features and advantages of the present invention will become apparent to one skilled in the art upon consideration of the following description of the invention and the accompanying drawings, in which:

FIG. 1 is a sectional view of a first embodiment of a catheter assembly in accordance with the present invention;

FIG. 1A is an enlarged sectional view of a first portion of the catheter assembly of FIG. 1;

FIG. 1B is an enlarged sectional view of a second portion of the catheter assembly of FIG. 1;

FIG. 2 is a sectional view of the catheter assembly of FIG. 1 in a longitudinally extended condition;

FIG. 3 is a sectional view of the catheter assembly of FIG. 1 in a non-extended condition;

FIG. 4 is a sectional view of a second embodiment of a catheter assembly in accordance with the present invention showing the catheter assembly in a non-extended condition;

FIG. 5 is a sectional view of the catheter assembly of FIG. 4 in a longitudinally extended condition;

FIG. 10A is an enlarged sectional view of a portion of the catheter assembly of FIG. 10;

DETAILED DESCRIPTION

Figure 4A:
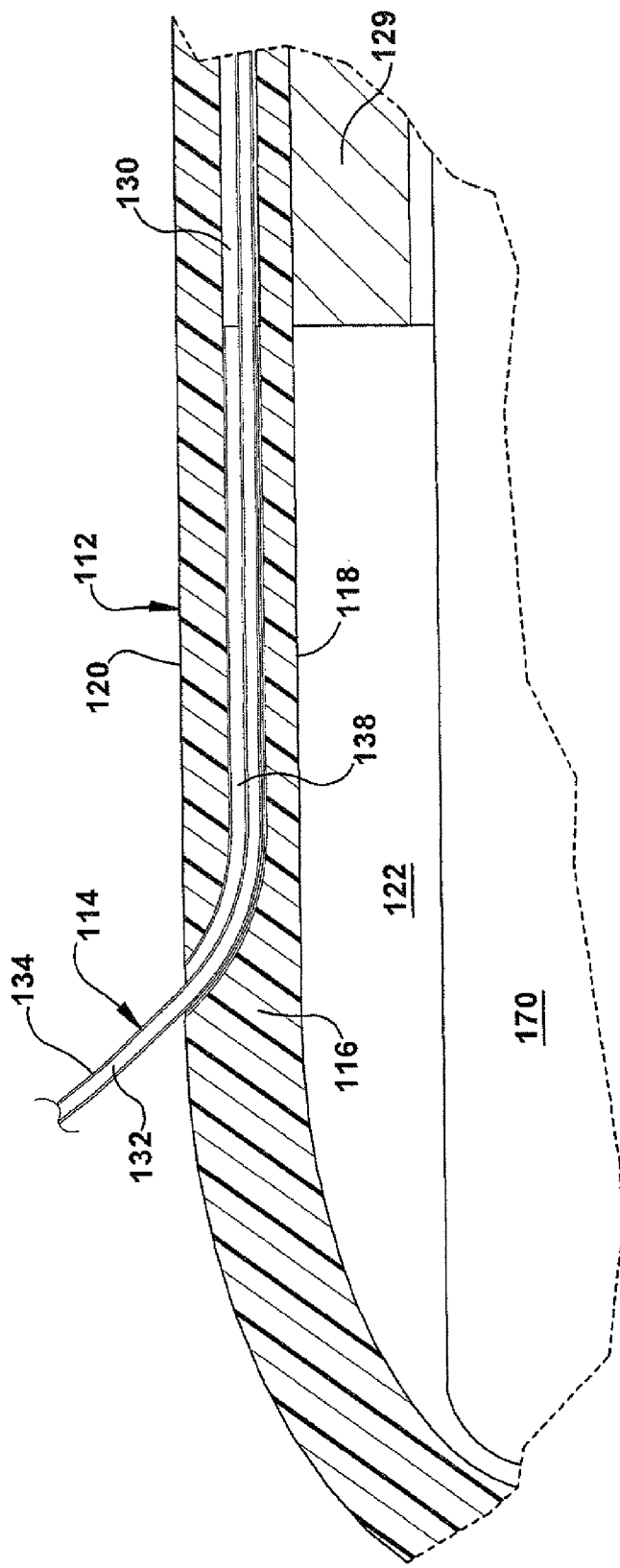
FIG. 4A is an enlarged sectional view of a portion of the catheter assembly of FIG. 4.

FIGS. 1 through 3 illustrate a catheter assembly 10, in accordance with an example of the present invention. The catheter assembly 10 includes a first or central catheter 12 and second or peripheral catheters 14, two of which are shown in FIG. 1. The central catheter 12 is made of a flexible and resilient bio-compatible material, such as a medical grade silicone elastomer, and includes a longitudinally extending, tubular wall 16. The tubular wall 16 includes a radially inner surface 18 and a radially outer surface 20. Both the inner surface 18 and the outer surface 20 extend substantially the entire length of the central catheter 12. The inner surface 18 defines a central lumen 22 that also extends substantially the entire length of the central catheter 12. The central lumen 22 is closed at a distal end 24 of the central catheter 12 by a thickened end portion 26 of the wall 16. The central lumen 22 is open at the opposite, proximal end 28 of the central catheter 12.

Tunnels or passages 30 are formed in the wall 16 of the central catheter 12 and extend generally lengthwise of the central catheter. Two passages 30 are shown in FIG. 1 at diametrically opposite positions about the circumference of the wall 16. The wall 16 of the central catheter 12 may include more or fewer such passages 30, as desired. Each of the passages 30 is substantially identical in construction to the other passages 30. The passages 30 will therefore be described with reference to the passage 30 located uppermost in FIG. 1, portions of which are shown in enlarged views in FIGS. 1A and 1B.

Each passage 30 receives an associated peripheral catheter 14. The peripheral catheter 14 is thus disposed in the wall 16 of the central catheter 12, radially outward of the inner surface 18 of the wall 16 and, for a portion of its length, radially inward of the outer surface 20 of the wall 16. This portion of the length of the peripheral catheter 14 extends lengthwise substantially parallel to the central catheter 12. As can be seen from FIGS. 1A and 1B, the outer diameter of the peripheral catheter 14 is smaller than the thickness of the wall 16 of the central catheter 12 and smaller than the diameter of the associated passage 30. The peripheral catheter 14 has a central lumen 32 and is formed of a bio-compatible material, such as polytetrafluoroethylene ("PTFE"), that has sufficient rigidity to penetrate a patient's tissue and has also has sufficient flexibility and resilience to withstand being deflected and then return to a non-deflected position.

As best seen in FIGS. 1 and 1A, a distal end portion 34 of the peripheral catheter 14 can project radially outward of the outer surface 20 of the wall 16 of the central catheter 12 near the distal end 24 of the central catheter. To facilitate such radially outward projection of the peripheral catheter 14, the passage 30 in the wall 16 of the central catheter 12 turns radially outward and opens onto the outer surface 20 of the wall 16. The material of which the peripheral catheter 14 is made is also given a predetermined shape in the distal end portion 34 of the peripheral catheter 14 in the form of an outwardly directed curve or hook.

As best seen in FIGS. 1 and 1B, a proximal end portion 36 of the peripheral catheter 14 communicates with the central lumen 22 of the central catheter 12 at a location spaced from both the distal end 24 and the proximal end 28 of the central catheter. To facilitate such communication between the peripheral catheter 14 and the central catheter 12, a short connector passage 38 extends radially inward from the passage 30 in the wall 16 and opens onto the inner surface 18 of the wall 16 of the central catheter. The proximal end portion 36 of the peripheral catheter 14 is inserted into the connector passage 38 until an end surface of the peripheral catheter is flush with the inner surface 18 of the wall 16. A biocompatible adhesive material 39 fixes the proximal end portion 36 of the peripheral catheter 14 to the wall 16 of the central catheter 12. The central lumen 32 of the peripheral catheter 14 is thus in fluid communication with the central lumen 22 of the central catheter 12.

As a result of the foregoing construction, fluid may flow along the central lumen 22 of the central catheter 12, then into the central lumen 32 in the proximal end portion 36 of the peripheral catheter 14, and further into the distal end portion 34 of the peripheral catheter. The distal end of the peripheral catheter 14 is open so that fluid may flow out of the open distal end of the peripheral catheter.

The portion of the central catheter 12 adjacent its proximal end 28 is received in a tubular male connector 40, such as a Luer lock connector. The male connector 40 has an enlarged head portion 42 and an opposite threaded portion 44. The head portion 42 of the male connector 40 has an outer surface 46 formed in a rounded hexagonal shape with raised, longitudinally extending ridges at the corners of the hexagonal shape to facilitate manipulation of the male connector. The threaded portion 44 of the male connector 40 has an outer surface 48 in which a screw thread 49 is formed. An inner surface 50 of the male connector 40 extends through both the head portion 42 and the threaded portion 44 of the male connector and defines a central passage in the male connector. The portion of the central catheter 12 adjacent the proximal end 28 is received in the central passage of the male connector 40 with the threaded portion 44 of the male connector adjacent the open proximal end 28 of the central catheter and with the head portion 42 of the male connector closer to the distal end 24 of the central catheter 12. A biocompatible adhesive 52 fixes the head portion 42 of the male connector 40 to the outer surface 20 of the wall 16 of the central catheter 12.

In use, as shown in FIG. 2, the threaded portion 44 of the male connector 40 is received in a female connector 54, such as a female Luer lock connector. Like the male connector 40, the female connector 54 has an enlarged head portion 56 and an opposite threaded portion 58. The head portion 56 of the female connector 54 has an outer surface 60 formed in a rounded hexagonal shape with raised, longitudinally extending ridges at the corners of the hexagonal shape to facilitate manipulation of the female connector. The threaded portion 58 of the female connector 54 has a cylindrical outer surface 62. An inner surface 64 of the female connector 54 extends through both the head portion 56 and the threaded portion 58 of the female connector and defines a central passage in the female connector. The inner surface 64 includes a radial step such that the central passage of the female connector 54 has a larger diameter adjacent the threaded portion 58 of the female connector and a smaller diameter adjacent the head portion 56 of the female connector. A screw thread 66 is formed in the inner surface 64 of the female connector 54 adjacent the threaded portion 58 of the female connector.

The threaded portion 44 of the male connector 40 is received in the threaded portion 58 of the female connector 54 with the screw thread 49 in the outer surface 48 of the threaded portion 44 engaging the screw thread 66 formed in the inner surface 64 of the female connector. An O-ring 68 is received against the inner surface 64 of the female connector 54 in the larger diameter portion of the central passage of the female connector between the end of the threaded portion 44 of the male connector 40 and the head portion 56 of the female connector.

When the catheter assembly 10 is to be inserted into tissue, such as cerebral tissue, of a patient, a stylet 70, which formed of a relatively strong and rigid material, such as stainless steel, is inserted into the catheter assembly. The stylet 70 is inserted into the central passage of the female connector 54, past the O-ring 68, and into the central lumen 22 of the central catheter 12 until a rounded distal end 72 of the stylet contacts the thickened end portion 26 of the wall 16 of the central catheter. After the distal end 72 of the stylet 70 contacts the thickened end portion 26, the stylet continues to be pushed into the central catheter 12 and against the thickened end portion 26 of the wall 16 of the central catheter. The continued pressure of the stylet 70 against the thickened end portion 26 of the wall 16 causes the resilient material of which the wall 16 is made to stretch and thereby causes the wall 16 to extend or distend axially or lengthwise into a longitudinally extended condition.

Longitudinal stretching of the wall 16 causes the outer diameter of the wall to decrease or be reduced, as can be seen in FIG. 2 by comparing the diameter of the middle portion of the wall with the portion adjacent to the male connector 40. Stretching of the wall 16 of the central catheter 12 also causes the distal end portions 34 of the peripheral catheters 14 to be withdrawn into the passages 30 in the wall 16, as can be seen in FIG. 2, because the proximal end portions 36 of the peripheral catheters 14 are fixed to the wall 16. As they are withdrawn into the passages 30, the distal end portions 34 of the peripheral catheters 14 are deflected from their outwardly curving, predetermined shape and are constrained in a generally straight configuration by the wall 16 of the central catheter 12. When the peripheral catheters 14 have been fully withdrawn or retracted into the wall 16 of the central catheter 12, the outer surface 20 of the wall 16 of the central catheter appears essentially smooth and uninterrupted. The wall 16 of the central catheter 12 thus functions as a sheath portion of the central catheter and covers the distal end portions 34 of the peripheral catheters 14.

The stylet 70 can then be used to insert the extended central catheter 12 and the peripheral catheters 14 into the tissue of a patient. To facilitate such use of the stylet 70, the female connector 54 may be screwed further onto the male connector 40 to cause radially inward bulging of the O-ring 68. Radially inward bulging of the O-ring 68 causes the O-ring to grip the outer surface of the stylet 70 tightly and thus to hold the stylet longitudinally in position in the extended central catheter 12. Because the outer diameter of the central catheter 12 has been reduced due to the lengthwise extension or distension of the central catheter, the opening that will be formed in the patient's tissue is smaller than it would be otherwise. Because the distal end portions 34 of the peripheral catheters 14 have been withdrawn into the wall 16 of the central catheter 12, the peripheral catheters do not interfere with the insertion of the central catheter into the patient's tissue. When the distal end 24 of the central catheter 12 is appropriately positioned in a patient's tissue, the stylet 70 is held so as to maintain the distal end of the central catheter in position. The female connector 54 may then be at least partially unscrewed from the male connector 40 so that the O-ring 68 no longer tightly grips the outer surface of the stylet 70. With the stylet 70 held in position and the O-ring 68 no longer tightly gripping the stylet, the resilience of the extended central catheter 12 pulls the proximal end 28 of the central catheter along the stylet toward the distal end 24 of the central catheter. The central catheter 12 thus returns resiliently to its initial, non-extended length while the distal end 24 of the central catheter remains in position.

When the central catheter 12 resiliently returns to its initial, non-extended length and the wall 16 of the central catheter resiliently likewise returns from its longitudinally extended condition to its initial, non-extended length, the distal end portions 34 of the peripheral catheters 14 are no longer withdrawn into the wall 16. The distal end portions 34 of the peripheral catheters 14 instead project from the outer surface 20 of the wall 16 of the central catheter 12 and again assume their outwardly curved, predetermined shape. As the distal end portions 34 of the peripheral catheters 14 assume their outwardly curved, predetermined shape, the peripheral catheters penetrate the patient's tissue and extend into the patient's tissue away from the central catheter 12 in a radial array. In addition, as the wall 16 of the central catheter 12 resiliently returns to its initial length, the outer diameter of the wall increases from its reduced condition back to its original dimension. The increase in the outer diameter of the wall 16 of the central catheter 12 causes the outer surface 20 of the wall 16 to press tightly against adjacent surfaces of the patient's tissue. The resulting close fit between the outer surface 20 of the wall 16 and the adjacent surfaces of the patient's tissue helps to prevent fluid introduced into the tissue by the peripheral catheters 14 from flowing back along the outer surface of the wall toward the proximal end 28 of the central catheter 12.

With the central and peripheral catheters 12 and 14 of the catheter assembly 10 appropriately positioned in the patient's tissue, therapeutic treatment of the tissue with a bioactive material can begin. To introduce the bioactive material, the stylet 70 is withdrawn entirely from the central lumen 22 of the central catheter and the catheter assembly 10 and from the female connector 54. The threaded portion 58 of the female connector 54 is then unscrewed from the threaded portion 44 of the male connector 40 and the O-ring 68 is removed. A length of tubing 74 is inserted into the central passage of the female connector 54 until an enlarged distal end 76 of the tubing 74 engages the head portion 56 of the female connector. When the female connector 54 is again screwed onto the male connector 40, the enlarged distal end 76 of the tubing 74 is trapped in the central passage of the female connector between the threaded portion 44 of the male connector and head portion 56 of the female connector, as shown in FIG. 3. As the male and female connectors 40 and 54 are screwed together more tightly, the tubing 74 is sealed against the connectors and against the proximal end 28 of the central catheter 12.

A proximal end (not shown) of the tubing 74 is then attached to a device (not shown), such as a pump, for delivering a fluid, such as a liquid, under pressure to the catheter assembly 10 and thus into a patient's tissue. The fluid contains a bioactive material, such as a pharmaceutical material, and is delivered from the tubing 74 into the central lumen 22 of the central catheter 12. From the central catheter 12, the fluid containing the bioactive material is delivered through the inner surface 18 of the wall 16 of the central catheter into the central lumens 32 of the proximal end portions 36 of the peripheral catheters 14. The fluid flows along the central lumens 32 of the peripheral catheters 14 until it reaches the open ends of the distal end portions 34 of the peripheral catheters and is thereby introduced into the patient's tissue. When the patient's treatment is completed, the catheter assembly 10 may be removed by disconnecting the tubing 74 from the catheter assembly, reintroducing the stylet 70 into the catheter assembly to extend or distend the central catheter 12, and then withdrawing the catheter assembly and stylet from the patient's tissue.

FIGS. 4 through 5 illustrate a catheter assembly 100 that is constructed in accordance with a second example of the present invention. The catheter assembly 100 includes a first or central catheter 112 and second or peripheral catheters 114, two of which are shown in FIGS. 4 and 5. The central catheter 112 is made of a flexible and resilient bio-compatible material, such as such as a medical grade silicone elastomer, and includes a longitudinally extending, tubular wall 116. The tubular wall 116 includes a radially inner surface 118 and a radially outer surface 120. Both the inner surface 118 and the outer surface 120 extend substantially the entire length of the central catheter 112. The outer surface 120 is separated from the inner surface 118 by a greater distance in a middle portion of the central catheter 112 than adjacent its distal and proximal ends 124 and 128, respectively. As a consequence, the wall 116 has a greater thickness in a middle portion 121 of its length than at either end of the wall.

The inner surface 118 of the wall 116 defines a central lumen 122 that extends substantially the entire length of the central catheter 112. The central lumen 122 is closed at the distal end 124 of the central catheter 112 by a thickened end portion 126 of the wall 116. The central lumen 122 is open at the opposite, proximal end 128 of the central catheter 112. A tubular stopper element 129 is disposed in the central lumen 122 of the central catheter 112 adjacent an end of the thickened middle portion 121 of the wall 116 closest to the distal end 124 of the central catheter. The stopper element 129, which may be formed of medical grade tubing, is secured to the inner surface 118 of the wall 116 by a biocompatible adhesive (not shown).

As best shown in FIG. 4A, tunnels or passages 130 are formed in the wall 116 of the central catheter 112 and extend generally lengthwise of the central catheter. Two passages 130 are shown in FIGS. 4 and 5 at diametrically opposite positions about the circumference of the wall 116. The wall 116 of the central catheter 112 may include more or fewer such passages 130, as desired. Each of the passages 130 is substantially identical in construction to the other passages 130. Like the passages 30 of the catheter assembly 10 shown in FIGS. 1-3, each of the passages 130 receives an associated peripheral catheter 114. The peripheral catheters 114 are thus disposed in the wall 116 of the central catheter 112, radially outward of the inner surface 118 of the wall 116 and, for a major portion of their lengths, radially inward of the outer surface 120 of the wall 116. This portion of the lengths of the peripheral catheters 114 extends lengthwise substantially parallel to the central catheter 112. As can be seen from FIG. 4A, the outer diameter of each of the peripheral catheters 114 is smaller than the thickness of the wall 116 of the central catheter 112 and smaller than the diameter of the associated passage 130. The peripheral catheter 114 has a central lumen 132 and is formed of a biocompatible material, such as PTFE, that has sufficient rigidity to penetrate a patient's tissue and also has sufficient flexibility and resilience to withstand being deflected and then return to a non-deflected position.

As best seen in FIGS. 4 and 4A, a distal end portion 134 of each peripheral catheter 114 can project radially outward of the outer surface 120 of the wall 116 of the central catheter 112 near the distal end 124 of the central catheter. To facilitate such radially outward projection of the peripheral catheter 114, the passage 130 in the wall 116 of the central catheter 112 curves radially outward and opens onto the outer surface 120 of the wall 116. A short length of tubing 138, such as PTFE tubing, is positioned in the radially curved portion of the passage 130 and is bonded to the wall 116 to act as a bearing surface for sliding movement of the peripheral catheter 114 relative to the wall 116. The distal end portion 134 of the peripheral catheter 114 is given a predetermined shape in the form of an outwardly directed curve or hook.

Unlike the peripheral catheters 14 of the catheter assembly 10, the central lumen 132 of the proximal end portion 136 of each peripheral catheter 114 does not communicate with the central lumen 122 of the central catheter 112. Instead, the proximal end portion 136 of each peripheral catheter 114 projects radially outward of the outer surface 120 of the wall 116 of the central catheter 112 near the proximal end 128 of the central catheter. The proximal end portion 136 of each peripheral catheter 114 is associated with a fluid inlet port or injection port assembly 180, which receives the proximal end portion of its associated peripheral catheter.

Each injection port assembly 180 includes a sleeve portion 182 and connector portion 184, such as a Luer lock connector.

The sleeve portion 182 and connector portion 184 of each injection port assembly 180 are joined to one another and may be formed in one piece. The sleeve portion 182 of each injection port assembly 180 is elongated and extends between its associated connector portion 184 and an area on the outer surface 120 of the wall 116 of the central catheter 112 from which the proximal end portion 136 of the associated peripheral catheter 114 projects. The sleeve portion 182 surrounds and is bonded to the proximal end portion 136 of the associated peripheral catheter 114 and helps to protect the proximal end portion. The sleeve portion 182 is also adhesively bonded or otherwise secured to the outer surface 120 of the wall 116 of the central catheter 112, thereby fixing the proximal end portion 136 of the associated peripheral catheter 114 to the wall 116 of the central catheter.

The proximal end portion 136 of each peripheral catheter 114 extends into the connector portion 184 of its associated injection port assembly 180. The central lumen 132 of the peripheral catheter 114 communicates with a central lumen 186 in the connector portion 184 of the injection port assembly 180. An outer surface 188 of the connector portion 184 is threaded to facilitate attachment of a second connector (not shown) and tubing (not shown) for delivering a fluid to the connector portion and thus to the peripheral catheter 114. Such a fluid may flow along the central lumen 132 of the peripheral catheter 114 from its proximal end portion 136 into the distal end portion 134 of the peripheral catheter. The distal end of the peripheral catheter 114 is open so that fluid may flow out of the open distal end of the peripheral catheter.

The portion of the central catheter 112 adjacent the proximal end 128 is received in a tubular male connector 140, such as a male Luer lock connector. The male connector 140 has a head portion 142 and an opposite threaded portion 144. The head portion 142 of the male connector 140 has an outer surface 146 formed for manual manipulation to facilitate attachment of another connector, as shown in FIG. 5. The threaded portion 144 of the male connector 140 has an outer surface 148 in which a screw thread 149 is formed. An inner surface 150 of the male connector 140 extends through both the head portion 142 and the threaded portion 144 of the male connector and defines a central passage in the male connector. The portion of the central catheter 112 adjacent its proximal end 128 is received in the central passage of the male connector 140 with the threaded portion 144 of the male connector adjacent the open proximal end of the central catheter and with the head portion 142 of the male connector closer to the distal end 124 of the central catheter 112. A biocompatible adhesive 152 fixes the head portion 142 of the male connector 140 to the outer surface 120 of the wall 116 of the central catheter 112.

When the catheter assembly 100 is ready to be inserted into tissue, such as cerebral tissue, of a patient, a stylet 170 formed of a relatively strong and rigid material, such as stainless steel, is inserted into the catheter assembly. Near its rounded distal end 172, the stylet 170 has an annular, radially extending surface 171 that provides a step encircling the stylet. Near its proximal end, the stylet 170 is encircled by an annular stroke limiter 173 that is fixed to the stylet. The stylet 170 is inserted into the central passage of the male connector 140 and then into the central lumen 122 of the central catheter 112 until the radially extending surface 171 contacts the stopper element 129 secured to the inner surface 118 of the wall 116 of the central catheter.

After the radially extending surface 171 of the stylet 170 contacts the stopper element 129, the stylet continues to be pushed into the central catheter 112 and against the stopper element until the stroke limiter 173 contacts the proximal end 128 of the central catheter and the adjacent end of the threaded portion 144 of the male connector 140. The continued pressure of the stylet 170 against the stopper element 129 causes the resilient material of which the wall 116 is made to stretch and thereby causes the wall 116 to extend or distend axially or lengthwise into a longitudinally extended condition. This stretching of the wall 116 occurs primarily in the thickened middle portion 121 of the wall because the stopper element 129 is bonded to the inner surface 118 of the wall and effectively transfers the force applied by the stylet to the wall 116 adjacent the end of the middle portion closest to the distal end 124 of the central catheter 112. Adjacent the opposite end of the thickened middle portion 121 of the wall 116, the peripheral catheters 114 are adhesively bonded to the sleeve portions 182 of the injection port assemblies 180 and are also adhesively bonded to the surface of the wall 116 that defines the passage 130. These adhesive bonds effectively restrict or prevent stretching of the wall 116 adjacent the proximal end 128 of the central catheter 112.

Stretching of the wall 116 causes the outer diameter of the wall to decrease or be reduced, as can be seen in FIG. 5 by comparing the diameter of the middle portion 121 of the wall with the portion adjacent the stopper element 129. Stretching of the wall 116 of the central catheter 112 also causes the distal end portions 134 of the peripheral catheters 114 to be withdrawn into the passages 130 in the wall 116, as shown in FIG. 5, because the proximal end portions 136 of the peripheral catheters are fixed to the injection port assemblies 180 and to the surfaces of the wall 116 that define the passages. As they are withdrawn into the passages 130, the distal end portions 134 of the peripheral catheters 114 are deflected from their outwardly curving, predetermined shape and are constrained in a generally straight configuration by the wall 116 of the central catheter 112. When the peripheral catheters 114 have been fully withdrawn or retracted into the wall 116 of the central catheter 112, the outer surface 120 of the wall 116 of the central catheter appears essentially smooth and uninterrupted. The wall 116 of the central catheter 112 thus functions as a sheath portion of the central catheter and covers the distal end portions 134 of the peripheral catheters 114.

When the stylet 170 reaches the end of its stroke, as determined by contact between the stroke limiter 173 and the proximal end 128 of the central catheter and the adjacent end of the threaded portion 144 of the male connector 140, the stylet may be secured in place to facilitate coordinated manipulation of the stylet and the catheter assembly 100. As best seen in FIG. 5, the threaded portion 144 of the male connector 140 may be received in a female connector 154. The female connector 154 has an enlarged head portion 156 and an opposite threaded portion 158. The head portion 156 of the female connector 154 has an outer surface 160 formed in a rounded hexagonal shape with raised, longitudinally extending ridges at the corners of the hexagonal shape to facilitate manipulation of the female connector. The threaded portion 158 of the female connector 54 has a cylindrical outer surface 162. An inner surface 164 of the female connector 154 extends through both the head portion 156 and the threaded portion 158 of the female connector and defines a central passage in the female connector. The inner surface 164 includes a radial step such that the central passage of the female connector 154 has a larger diameter adjacent the threaded portion 158 of the female connector and a smaller diameter adjacent the head portion 156 of the female connector. A screw thread 166 is formed in the inner surface 164 of the female connector 154 adjacent the threaded portion 158 of the female connector.

The threaded portion 144 of the male connector 140 is received in the threaded portion 158 of the female connector 154 with the screw thread 149 in the outer surface 148 of the threaded portion 144 engaging the screw thread 166 formed in the inner surface 164 of the female connector. An annular washer (not shown), which may be formed of PTFE, for example, may be received against the inner surface 164 of the female connector 154 in the larger diameter portion of the central passage of the female connector between the end of the threaded portion 144 of the male connector 140 and the head portion 156 of the female connector.

When the female connector 154 is screwed onto the male connector 140, the stroke limiter 173 of the stylet 170 is trapped between the threaded portion 144 of the male connector and head portion 156 of the female connector. The stylet 170 and the catheter assembly 100 then tend to move more consistently as a single unit and can be manipulated more easily and accurately. In particular, the stylet 170 can then be used to insert the extended central catheter 112 and the peripheral catheters 114 into the tissue of a patient. Because the outer diameter of the central catheter 112 has been reduced due to the lengthwise extension or distension of the central catheter, the opening formed in the patient's tissue is smaller than it would be otherwise. Because the distal end portions 134 of the peripheral catheters 114 have been withdrawn into the wall 116 of the central catheter, the peripheral catheters do not interfere with the insertion of the central catheter into the patient's tissue. When the distal end 124 of the central catheter 112 is appropriately positioned in a patient's tissue, the stylet 170 is held so as to maintain the distal end of the central catheter in position. The female connector 154 may then be unscrewed from the male connector 140 so that the stroke limiter 173 of the stylet 170 is no longer trapped between the threaded portion 144 of the male connector and head portion 156 of the female connector. With the stylet 70 held in position and the stroke limiter 173 no longer trapped between the male and female connectors 140 and 154, respectively, the resilience of the extended central catheter 112 pulls the proximal end 128 of the central catheter along the stylet toward the distal end 124 of the central catheter. The central catheter 112 thus returns resiliently to its initial, non-extended length while the distal end 124 of the central catheter remains in position.

When the central catheter 112 resiliently returns to its initial, non-extended length and the wall 116 of the central catheter likewise resiliently returns from its longitudinally extended condition to its initial, non-extended length, the distal end portions 134 of the peripheral catheters 114 are no longer withdrawn into the wall 116. The distal end portions 134 of the peripheral catheters 114 instead project from the outer surface 120 of the wall 116 of the central catheter and assume their outwardly curved, predetermined shape. As the distal end portions 134 of the peripheral catheters 114 assume their outwardly curved, predetermined shape, the peripheral catheters 114 penetrate the patient's tissue and extend into the patient's tissue away from the central catheter 112 in a radial array. In addition, as the wall 116 of the central catheter 112 resiliently returns to its initial length, the outer diameter of the wall, particularly the middle portion 121, increases from its reduced condition back to its original dimension. The increase in the outer diameter of the wall 116 of the central catheter 112 causes the outer surface 120 of the wall 116 to press tightly against adjacent surfaces of the patient's tissue. The resulting close fit between the outer surface 120 of the wall 116 and the adjacent surfaces of the patient's tissue helps to prevent fluid introduced into the tissue by the peripheral catheters 114 from flowing back along the outer surface of the wall toward the proximal end 128 of the central catheter 112.

With the central and peripheral catheters 112 and 114 of the catheter assembly 10 appropriately positioned in the patient's tissue, therapeutic treatment of the tissue with a bioactive material can begin. To introduce the bioactive material, the stylet 170 is withdrawn entirely from the central lumen 122 of the central catheter 112 and the catheter assembly 100 and from the male connector 140. The threaded outer surface 188 of the connector portion 184 of each injection port assembly 180 is connected with a connector (not shown) and the distal end of a length of tubing (not shown). A proximal end (not shown) of the tubing is attached to a device (not shown), such as a pump, for delivering a fluid, such as a liquid. The fluid contains a bioactive material, such as a pharmaceutical material, and is delivered from the tubing into the central lumen 186 of the connector portion 184 of the injection port assembly 180 and then into the central lumen 132 of the associated peripheral catheter 114. The fluid flows along the central lumen 132 of the peripheral catheter 114 until it reaches the open end of the distal end portion 134 of the peripheral catheter and is thereby introduced into the patient's tissue. When the patient's treatment is completed, the catheter assembly 100 may be removed by reintroducing the stylet 170 into the catheter assembly to extend or distend the central catheter 112 and then withdrawing the catheter assembly from the patient's tissue.

In one particular embodiment of a catheter in accordance with FIGS. 4 through 5, the central catheter 112 is formed of a medical grade silicone rubber, which is available as product number MED 4901 from Nusil Silicone Technology of Carpinteria, Calif., U.S.A. The nominal outside diameter of the central catheter 112 is between about 2.0 mm and about 2.5 mm. The peripheral catheters 114 are formed of PTFE medical grade tubing with a nominal inside diameter of about 0.203 mm (0.008 inches), a wall thickness of about 0.076 mm (0.003 inches), and a nominal outside diameter of about 0.356 mm (0.014 inches). The distal end portions 134 of the peripheral catheters 114 project outward from the outer surface 120 of the wall 116 of the central catheter 112 a distance from about 10 mm to about 20 mm. In areas where the peripheral catheters 114 are to be bonded to the central catheter 112 or another element of the catheter assembly 100, the outer surfaces of the peripheral catheters are etched to enhance bonding and a silicone adhesive, such as product number 1137 from Nusil Silicone Technology of Carpinteria, Calif., U.S.A., is used. The numerical values set forth above and other numerical values set forth in the present application are given by way of example only and other values may be used with satisfactory results.

FIGS. 6 through 9 illustrate a catheter assembly 200 that is constructed in accordance with a third example of the present invention. The catheter assembly 200 includes a first or central catheter 212 and second or peripheral catheters 214, which are shown schematically in FIGS. 7-9. The central catheter 212 is made of a flexible and resilient bio-compatible material, such as a medical grade silicone elastomer, and includes a wall 216. The wall 216 includes a radially inner surface 218 and a radially outer surface 220. Both the inner surface 218 and the outer surface 220 extend substantially throughout the central catheter 212. The inner surface 218 defines a central lumen 222 that also extends substantially throughout the central catheter 212.

Figure 7:
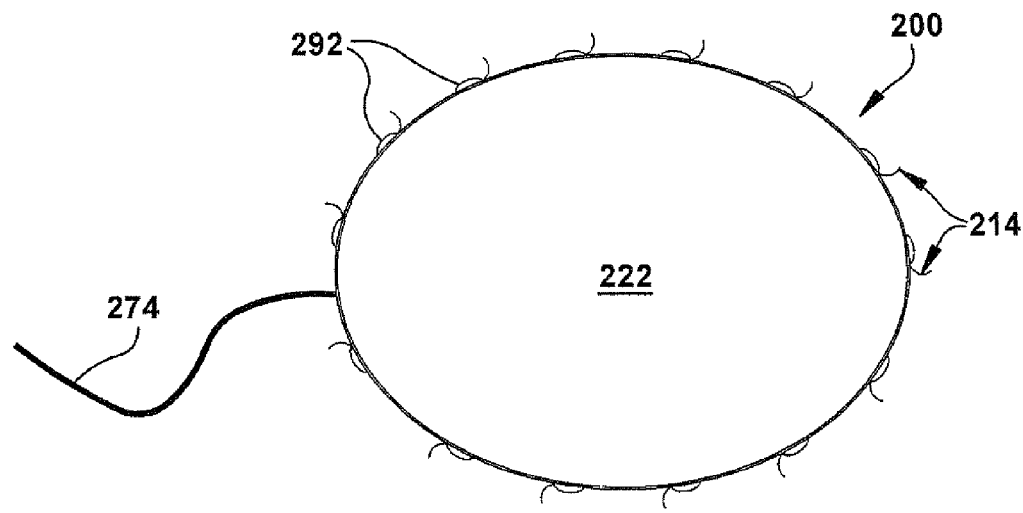
FIG. 7 is a schematic view of the catheter assembly of FIG. 6 in an extended condition.

The central lumen 222 is closed at a distal end 224 of the central catheter 212 by a portion of the wall 216. The central lumen 222 is open at the opposite, proximal end 228 of the central catheter 212. The open proximal end 228 of the central lumen 222 is connected to and communicates with a length of tubing 274. The tubing 274 delivers a fluid to the central lumen 222 for inflating or distending the central catheter 212. When inflated or distended, as shown in FIG. 7, the central catheter 212 resembles a balloon and can occupy a space or volume that has a relatively large radial dimension. The central catheter 212 is thus suitable for use in a tissue cavity, such as a resection cavity from which a tumor has been surgically removed.

Figure 8:
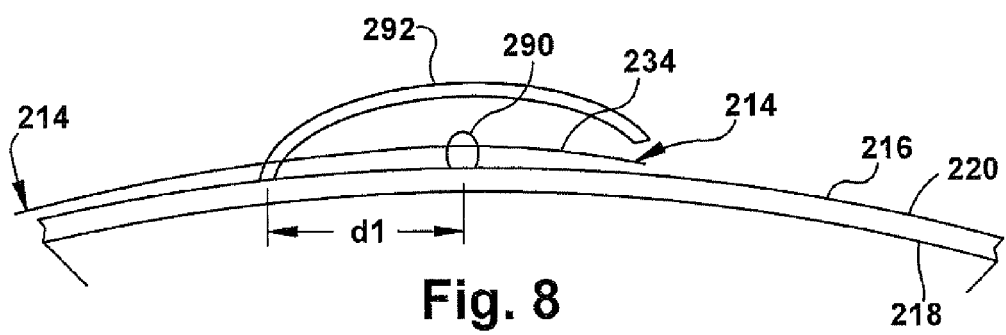
FIG. 8 is an enlarged schematic view of a portion of the catheter assembly of FIG. 6.
Figure 9:
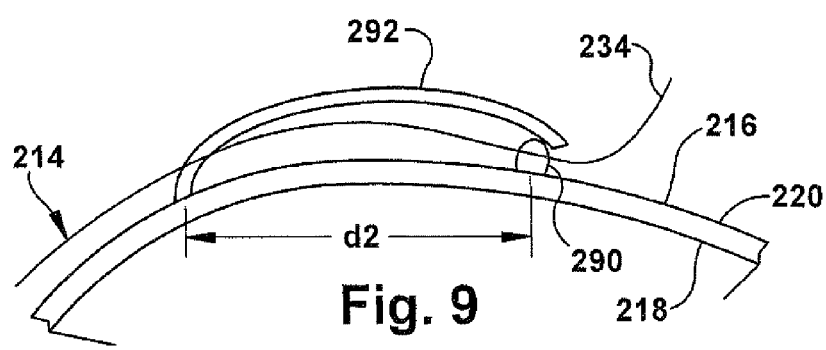
FIG. 9 is an enlarged schematic view of a portion of the catheter assembly of FIG. 7.

Unlike the embodiments of FIGS. 1-3 and FIGS. 4-5, tunnels or passages need not be formed in the wall 216 of the central catheter 212 to receive the peripheral catheters 214. Instead, the peripheral catheters 214 may be positioned against the outer surface 220 of the wall 216 of the central catheter 212, as shown in FIGS. 8 and 9. Each peripheral catheter 214 is thus disposed radially outward of the inner surface 118 of the wall 116 and radially outward of the outer surface 220 of the wall 216. Each peripheral catheter also extends lengthwise in the same general direction as the central catheter 212. As indicated in FIGS. 8 and 9, the outer diameter of each peripheral catheter 214 is smaller than the thickness of the wall 216 of the central catheter 212. The peripheral catheter 214 has a central lumen (not shown) and is formed of a material, such as a bio-compatible PTFE, that has sufficient rigidity to penetrate a patient's tissue and has also has sufficient flexibility and resilience to withstand being deflected and then return to a non-deflected position.

As best seen in FIG. 9, a distal end portion 234 of each peripheral catheter 214 can project radially outward of the outer surface 220 of the wall 216 of the central catheter 212. To facilitate such radially outward projection of the peripheral catheter 214, the distal end portion 234 of the peripheral catheter is given a predetermined shape in the form of an outwardly directed curve or hook. The distal end portion 234 of each peripheral catheter 214 is also fixed or immovably attached to a point on the outer surface 220 of the wall 216 of the central catheter 212 by an associated attachment 290, such as a small mass of silicone elastomer bonded to the outer surface. Each peripheral catheter 214 has its own, individual attachment point and associated attachment 290.

To constrain the distal end portion 234 of each peripheral catheter 214 and maintain the distal end portion against the wall 216 of the central catheter, the distal end portion is covered by an associated sheath 292. Each sheath 292 is fixed or immovably attached at one end to the outer surface 220 of the wall 216 of the central catheter 212 at a point or along a line adjacent to but spaced apart from the attachment 290 for an associated peripheral catheter 214. The length of each sheath 292 is sufficient that the sheath covers the entire length of the distal end portion 234 of an associated peripheral catheter 214. Each sheath 292 is attached at one or more points or on a line along its length to the outer surface 220 of the wall 216 of the central catheter 212 using a releasable adhesive or other detachable attachment mechanism (not shown) to help maintain the distal end portion 234 of the associated peripheral catheter 214 against the wall 216 of the central catheter.

The peripheral catheters 214 do not communicate with the central lumen 222 of the central catheter 212. Instead, the proximal end portion (not shown) of each peripheral catheter 214 is connected to a device (not shown), such as pump, for delivering a fluid, such as a liquid, under pressure to the catheter assembly 200 and thus into a patient's tissue. The fluid contains a bioactive material, such as a pharmaceutical material, and is delivered to the each of the peripheral catheters 214. Such a fluid may flow along the central lumen (not shown) of the peripheral catheter 214 from adjacent its proximal end portion (not shown) into the distal end portion 234 of the peripheral catheter. The distal end of the peripheral catheter 214 is open so that fluid may flow out of the open distal end of the peripheral catheter.

Figure 6:
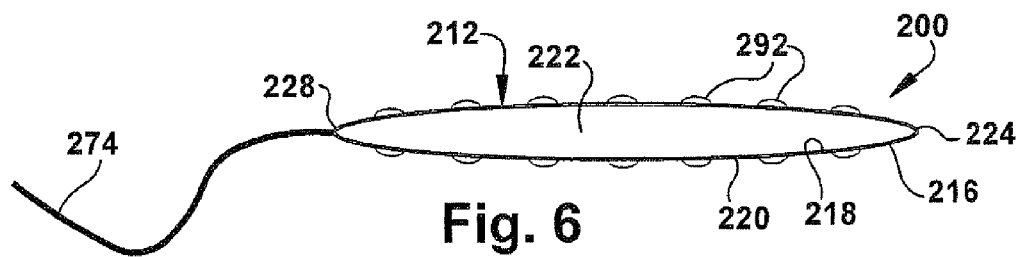
FIG. 6 is a schematic view of a third embodiment of a catheter assembly in accordance with the present invention showing the catheter assembly in a non-extended condition.

In use, the central catheter 212 is introduced into a cavity, such as a resection cavity, in the tissue of a patient. The central catheter 212 is introduced into the tissue cavity in an uninflated or partially inflated or distended condition, as shown in FIG. 6. In this condition, the distal end portions 234 of the peripheral catheters 214 lie against the outer surface 220 of the wall 216 of the central catheter 212 and are covered by their associated sheaths 292, as shown in FIG. 8. When the central catheter 212 is appropriately positioned, fluid is introduced into the central lumen 222 of the central catheter to inflate the central catheter. As the central catheter 212 inflates, the wall 216 of the central catheter resiliently stretches or distends. As the wall 216 of the central catheter 212 resiliently distends or extends, the central catheter fills the cavity in the tissue of the patient and the distal end portions 234 of the peripheral catheters 214 are moved closer to the tissue surrounding and defining the cavity in the tissue.

In addition, as the wall 216 of the central catheter 212 resiliently extends or distends and the central catheter inflates, the distance between the fixed attachment point of each sheath 292 and the attachment 290 for the distal end portion 234 of its associated peripheral catheter 214 increases from a first distance (designated "d1" in FIG. 8) to a second, greater distance (designated "d2" in FIG. 9). The movement of the fixed attachment point of each sheath 292 relative to other points on the outer surface 220 of the wall 216 of the central catheter 212 causes the releasable adhesive or other detachable attachment mechanism (not shown) along the length of the sheath to release or detach from the outer surface 220 of the wall 216. The sheath 292 is thereby allowed to move from a position covering and constraining the distal end portion 234 of its associated peripheral catheter 214. The sheath 292 may be viewed as effectively withdrawn from a position covering and constraining the distal end portion 234 of its associated peripheral catheter 214. Alternatively, the distal end portion 234 of the associated peripheral catheter 214 may be viewed as effectively pulled by its associated attachment 290 away from the sheath 292. Regardless of the point of view, the distal end portions 234 of the peripheral catheters 214 are left free to project away from the outer surface 220 of the wall 216 of the central catheter 212 and assume their outwardly curved, predetermined shape. As the distal end portions 234 of the peripheral catheters 214 assume their outwardly curved, predetermined shape, the peripheral catheters 214 penetrate the patient's tissue and extend into the patient's tissue away from the central catheter 212 in a radial array.

With the central and peripheral catheters 212 and 214 of the catheter assembly 200 appropriately positioned in the patient's tissue, therapeutic treatment of the tissue with a bioactive material can begin. To introduce the bioactive material, the pump or other device (not shown) attached to the proximal ends (not shown) of the peripheral catheters is actuated. A fluid, such as a liquid, containing a bioactive material, such as a pharmaceutical material, is delivered under pressure to the catheter assembly 200 and thus into the patient's tissue. The fluid is delivered into the central lumens (not shown) of the associated peripheral catheters 214. The fluid flows along the central lumens of the peripheral catheters 214 until it reaches the open ends of the distal end portions 234 of the peripheral catheters and is thereby introduced into the patient's tissue. When the patient's treatment is completed, the catheter assembly 200 may be removed by allowing the central catheter 212 to deflate and then withdrawing the catheter assembly from the patient's tissue.

Although the catheter assembly 200 of FIGS. 6-9 is illustrated and described as having its peripheral catheters 214 disposed outward of the outer surface 220 of its central catheter 212, the peripheral catheters could be disposed, in whole or in part, in the wall 216 of the central catheter between the inner and outer surfaces 218 and 220. With such a construction, the wall 216 could, in effect, be a sheath portion of the central catheter and could potentially replace the sheaths 292.

Figure 10:
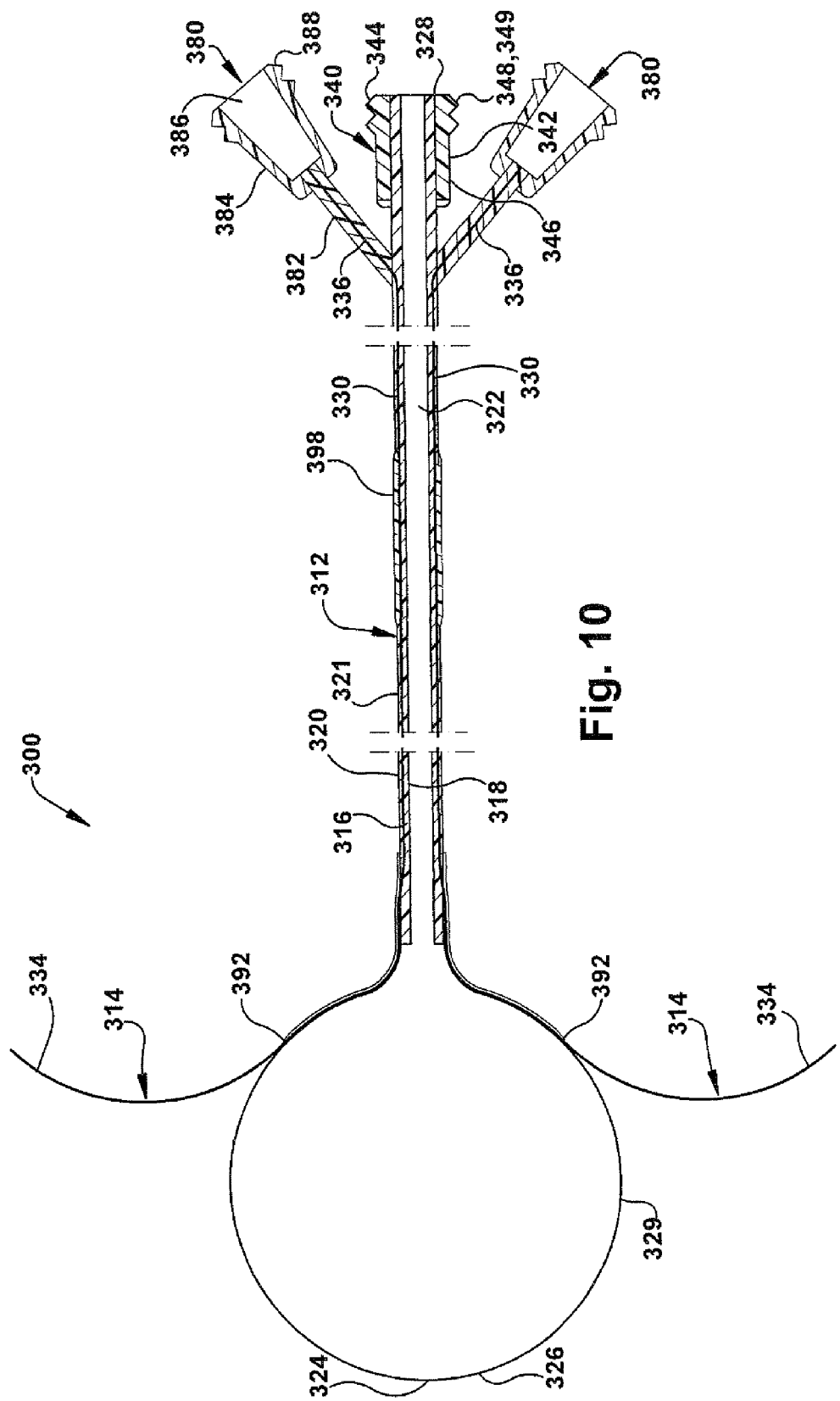
FIG. 10 is a sectional view of a fourth embodiment of a catheter assembly in accordance with the present invention showing the catheter assembly in an extended condition.
Figure 11:
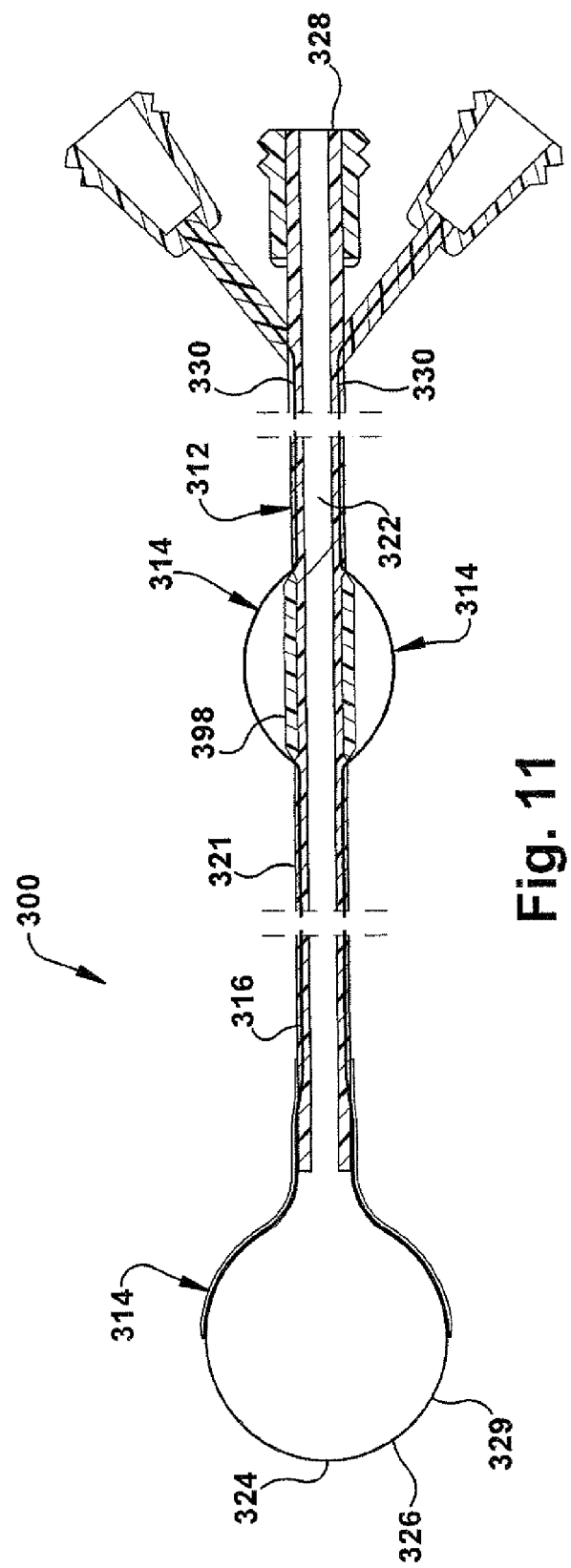
FIG. 11 is a sectional view of the catheter assembly of FIG. 10 in a non-extended condition.
Figure 12:
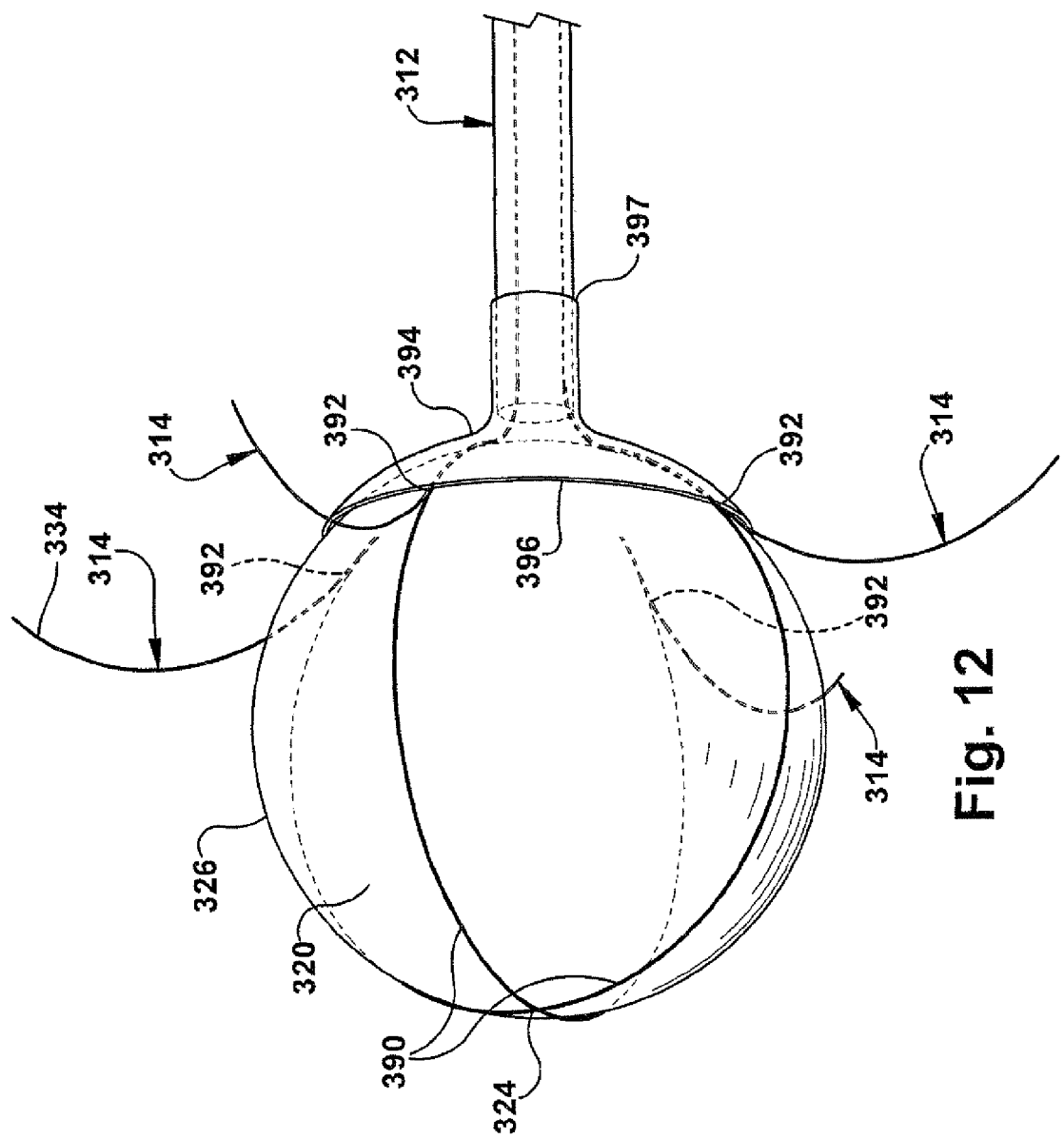
FIG. 12 is a perspective view of a portion of the catheter assembly of FIG. 10.

FIGS. 10 through 12 illustrate a catheter assembly 300 that is constructed in accordance with a fourth example of the present invention. The catheter assembly 300 includes a first or central catheter 312 and second or peripheral catheters 314, two of which are shown in FIGS. 10 and 11. The central catheter 312 is made of a flexible and resilient bio-compatible material, such as such as a medical grade silicone elastomer, and includes a longitudinally extending, tubular wall 316. The tubular wall 316 includes a radially inner surface 318 and a radially outer surface 320. Both the inner surface 318 and the outer surface 320 extend substantially the entire length of the central catheter 312.

The inner surface 318 of the wall 316 defines a central lumen 322 that extends substantially the entire length of the central catheter 312. The central lumen 322 is closed at the distal end 324 of the central catheter 312 by a thinned end portion 326 of the wall 316. The central lumen 322 is open at the opposite, proximal end 328 of the central catheter 312. The thinned end portion 326 of the wall 316 partially defines a balloon portion 329 of the central catheter 312 and the catheter assembly 300. In the thinned end portion 326 of the wall 316, the outer surface 320 of the wall 316 is separated from the inner surface 318 by a smaller distance than in a middle portion 321 of the length of the central catheter 312 and in a portion adjacent the proximal end 328 of the central catheter. As a consequence, the wall 316 has a greater thickness in the middle portion 321 of its length and adjacent its proximal end 328 than adjacent its distal end 324 and in the thinned portion 326.

The thinned end portion 326 of the wall 316 of the central catheter 312 is formed from a separate piece of flexible and resilient bio-compatible material, such as such as a medical grade silicone elastomer, and is secured to the middle portion 321 of the wall by, for example, a biocompatible adhesive material or radio frequency welding. Alternatively, the thinned end portion 326 may be formed in one piece with the middle portion 321 of the wall 316. The thinned end portion 326 of the wall 316 has a higher modulus of elasticity than the middle portion 321 of the length of the wall and the portion adjacent the proximal end 328 of the wall. As a result of the different moduli of elasticity and the previously described different thicknesses of the of the thinned end portion 326 and the middle portion 321 of the wall 316, when the central lumen 322 of the central catheter 312 is subjected to increased fluid pressure, such as a pressure greater than ambient atmospheric pressure, the thinned end portion 326 of the wall 316 tends to distend or extend to a greater extent than, for example, the middle portion 321.

As best shown in FIG. 10A, tunnels or passages 330 are formed in the wall 316 of the central catheter 312 and extend generally lengthwise of the central catheter. Two passages 330 are shown in FIGS. 10 and 11 at diametrically opposite positions about the circumference of the wall 316. The wall 316 of the central catheter 312 may include more or fewer such passages 330, as desired. Each of the passages 330 is substantially identical in construction to the other passages 330. Like the passages 130 of the catheter assembly 100 shown in FIGS. 4-5, each of the passages 330 receives an associated peripheral catheter 314. The peripheral catheters 314 are thus disposed in the wall 316 of the central catheter 312, radially outward of the inner surface 318 of the wall 316 and, for a major portion of their lengths, radially inward of the outer surface 320 of the wall 316. This portion of the lengths of the peripheral catheters 314 extends lengthwise substantially parallel to the central catheter 312. As can be seen from FIG. 10A, the outer diameter of each of the peripheral catheters 314 is smaller than the thickness of the middle portion 321 of the length of the wall 316 of the central catheter 312 and smaller than the diameter of the associated passage 330. Each peripheral catheter 314 has a central lumen 332 and is formed of a biocompatible material, such as PTFE, that has sufficient rigidity to penetrate a patient's tissue and also has sufficient flexibility and resilience to withstand being deflected and then return to a non-deflected position.

As best seen in FIGS. 10 and 10A, a distal end portion 334 of each peripheral catheter 314 can project radially outward of the outer surface 320 of the wall 316 of the central catheter 312 near the distal end 324 of the central catheter. To facilitate such radially outward projection of the peripheral catheter 314, the passage 330 in the wall 316 of the central catheter 312 angles radially outward and opens onto the outer surface 320 of the wall 316. The radially outward curvature of the passage 330 occurs adjacent the junction between the middle portion 321 of the wall 316 and the thinned end portion 326 of the wall. The distal end portion 334 of the peripheral catheter 314 is given a predetermined shape in the form of an outwardly directed curve or hook.

The proximal end portion 336 of each peripheral catheter 314 projects radially outward of the outer surface 320 of the wall 316 of the central catheter 312 near the proximal end 328 of the central catheter. The proximal end portion 336 of each peripheral catheter 314 is associated with a fluid inlet port or injection port assembly 380, which receives the proximal end portion of its associated peripheral catheter.

Each injection port assembly 380 includes a sleeve portion 382 and connector portion 384, such as a Luer lock connector. The sleeve portion 382 and connector portion 384 of each injection port assembly 380 are joined to one another and may be formed in one piece. The sleeve portion 382 of each injection port assembly 380 is elongated and extends between its associated connector portion 384 and an area on the outer surface 320 of the wall 316 of the central catheter 312 from which the proximal end portion 336 of the associated peripheral catheter 314 projects. The sleeve portion 382 surrounds and is bonded to the proximal end portion 336 of the associated peripheral catheter 314 and helps to protect the proximal end portion. The sleeve portion 382 is also adhesively bonded or otherwise secured to the outer surface 320 of the wall 316 of the central catheter 312, thereby fixing the proximal end portion 336 of the associated peripheral catheter 314 to the wall 316 of the central catheter.

The proximal end portion 336 of each peripheral catheter 314 extends into the connector portion 384 of its associated injection port assembly 380. The central lumen 332 of the peripheral catheter 314 communicates with a central lumen 386 in the connector portion 384 of the injection port assembly 380. An outer surface 388 of the connector portion 384 is threaded to facilitate attachment of a second connector (not shown) and tubing (not shown) for delivering a fluid to the connector portion and thus to the peripheral catheter 314. Such a fluid may flow along the central lumen 332 of the peripheral catheter 314 from its proximal end portion 336 into the distal end portion 334 of the peripheral catheter. The distal end of the peripheral catheter 314 is open so that fluid may flow out of the open distal end of the peripheral catheter.

The portion of the central catheter 312 adjacent the proximal end 328 is received in a tubular male connector 340, such as a male Luer lock connector. The male connector 340 has a head portion 342 and an opposite threaded portion 344. The head portion 342 of the male connector 340 has an outer surface 346 formed for manual manipulation to facilitate attachment of another connector (not shown), which, in turn, may be connected to and communicate with a length of tubing (not shown). The tubing delivers a fluid to the central lumen 322 for distending the thinned end portion 326 of the wall 316 of the central catheter 312 and inflating the central catheter. When distended, as shown in FIG. 10, the thinned end portion 326 resembles a balloon and can occupy a space or volume that has a relatively large radial dimension. The central catheter 312 is thus suitable for use in a tissue cavity, such as a resection cavity from which a tumor has been surgically removed.

Distension of the thinned end portion 326 of the wall 316 of the central catheter 312 also deploys the distal end portions 334 of the peripheral catheters 314. More specifically, as best shown in FIG. 12, one or more elongated pieces of material, such as threads, 390 extend across and are secured to the outer surface 320 of the thinned end portion 326 of the wall 316. The threads 390 are formed of a bio-compatible material that has a lower modulus of elasticity than the thinned end portion 326 of the wall 316. The threads 390 are thus less extensible than the thinned end portion 326 of the wall 316, but are flexible. The material of which the threads 390 are formed may be any material that is bio-compatible and that will produce threads that are less extensible than the thinned end portion 326 of the wall 316, including, for example, plastic, silicone, metal, and fabric. The material of the threads 390 need not be twisted like yarn or plaited or woven. The threads 390 may be elongated bands or strips of material.

Each thread 390 is secured to at least one point on the outer surface 320 of the thinned end portion 326, such as the distal end 324 of the central catheter 312. The thread 390 then extends in a direction away from the distal end 324 of the central catheter 312 toward the middle portion 321 of the wall 316. Near the middle portion 321 of the wall 316 of the central catheter 312 (when the central catheter is in a non-inflated or partially inflated condition, as, shown for example, in FIG. 11), the thread 390 is connected at a junction 392 to at least one peripheral catheter 314, thereby connecting the peripheral catheter 314 to the wall 316 of the central catheter. Each thread 390 may be secured to a single peripheral catheter 314. Alternatively, as shown in FIG. 12, each thread 390 may be secured at a first junction 392 to a first peripheral catheter 314, extend to the distal end 324 of the central catheter 312 along a circumferential path on the outer surface 320 of the thinned end portion, and then extend back to a second junction 392 at which the thread is secured to a second peripheral catheter 314 positioned diametrically opposite the first peripheral catheter.

Because the thread or threads 390 are secured to the thinned end portion 326 of the wall 316 of the central catheter 312, extension or distention of the thinned end portion 326 tends to pull the threads in a direction away from the middle portion 321 of the wall 316. As the threads 390 are pulled away from the middle portion 321 of the wall 316, the junctions 392 between the threads and the peripheral catheters 314, together with the distal ends 334 of the peripheral catheters, are similarly pulled in a direction away from the middle portion 321 of the wall. The curved or hooked distal end portions 334 of the peripheral catheters 314 are thereby deployed and pulled into the tissue surrounding the inflated or distended thinned end portion 326 of the wall 316. Distension or extension of the thinned end portion 326 of the wall 316 thus causes the distal end portions 334 of the peripheral catheters to be pulled by the threads 390 from a first, non-deployed position or condition to a second, deployed position or condition.

To help determine the area in which the distal end portions 334 of the peripheral catheters 314 enter the surrounding tissue, a cover or sheath 394 is disposed over the outer surface 320 of the thinned end portion 326 of the wall 316. As illustrated in FIG. 12, the sheath 394 is generally semi-spherical in shape with a large diameter open end 396 disposed away from the middle portion 321 of the wall 316 and a small diameter end 397 disposed adjacent to the middle portion of the wall 316. The small diameter end 397 of the sheath 394 is attached to the middle portion 321 of the wall 316 adjacent the junction between the middle portion and the thinned end portion 326 of the wall. The threads 390 and the distal end portions 334 of the peripheral catheters 314 extend between sheath 394 and the outer surface 320 of the thinned end portion 326 of the wall 316 of the central catheter 312. The sheath 394 may have a greater or lesser surface area than shown in FIG. 12 and may, therefore, cover or overlap the thinned end portion 326 to a greater or lesser extent than shown in FIG. 12.

The sheath 394 is formed of a material that has a lower modulus of elasticity than the material of which the thinned end portion 326 is made and tends to constrain the distal end portions 334 of the peripheral catheters 314. As the thinned end portion 326 of the wall 316 is distended, the threads 390 and the distal end portions 334 of the peripheral catheters 314 tend to be pulled from under the sheath 394 and may thus project away from the outer surface 320 of the wall 316 of the central catheter 312 and assume their outwardly curved, pre-determined shape. As the distal end portions 334 of the peripheral catheters 314 assume their outwardly curved, pre-determined shape, the peripheral catheters 314 penetrate the patient's tissue and extend into the patient's tissue away from the central catheter 312 in a radial array.

In use, the central catheter 312 of the catheter assembly 300 is introduced into a cavity, such as a resection cavity, in the tissue of a patient. The central catheter 312 is introduced into the tissue cavity in an uninflated or partially inflated condition, as shown in FIG. 11, with the thinned end portion 326 of the wall 316 either not distended or partially distended. In this condition, the distal end portions 334 of the peripheral catheters 314 lie against the outer surface 320 of the thinned end portion 326 of the wall 316 of the central catheter 312 and are covered by the sheath 394. When the central catheter 312 is appropriately positioned, fluid is introduced into the central lumen 322 of the central catheter to inflate or further inflate the central catheter and extend or distend the thinned end portion 326 of the wall 316 of the central catheter. As the central catheter 312 inflates, the thinned end portion 326 of the wall 316 of the central catheter resiliently stretches or distends. As the thinned end portion 326 of the wall 216 resiliently distends or extends, the central catheter 312 fills the cavity in the tissue of the patient and the distal end portions 334 of the peripheral catheters 314 are moved closer to the tissue surrounding and defining the cavity in the tissue.

In addition, as the central catheter 312 inflates and the wall 316 of the central catheter resiliently distends or extends, the threads 390 and the distal end portions 334 of the peripheral catheters 314 are pulled from under the sheath 394 so that the distal end portions 334 can project away from the outer surface 320 of the wall 316 and assume their outwardly curved, predetermined shape. As the distal end portions 334 of the peripheral catheters 314 assume their outwardly curved, pre-determined shape, the peripheral catheters 314 penetrate the patient's tissue and extend into the patient's tissue away from the central catheter 312 in a radial array.

With the central and peripheral catheters 312 and 314 of the catheter assembly 300 appropriately positioned in the patient's tissue, therapeutic treatment of the tissue with a bioactive material can begin. To introduce the bioactive material, a pump or other device (not shown) connected to the tubing (not shown) attached to the injection port assemblies 380 of the peripheral catheters 314 is actuated. A fluid, such as a liquid, containing a bioactive material, such as a pharmaceutical material, is delivered under pressure to the catheter assembly 300 and thus into the patient's tissue. The fluid is delivered into the central lumens 332 of the associated peripheral catheters 314. The fluid flows along the central lumens 332 of the peripheral catheters 314 until it reaches the open ends of the distal end portions 334 of the peripheral catheters and is thereby introduced into the patient's tissue.

When the patient's treatment is completed, the catheter assembly 300 may be removed by first allowing the central catheter 312 to deflate. To ensure that the peripheral catheters 314 are withdrawn from the patient's tissue and again covered by the sheath 394, resilient devices 398, such as elastic bands or springs, may be secured to the peripheral catheters in the middle portion 321 of the length of the wall 316 closer to the proximal end 328 than to the distal end 324 of the central catheter 312. As shown in FIG. 10, the resilient devices 398 may be stretched and flattened against the middle portion 321 of the wall 316 of the central catheter 312 when the thinned end portion 326 of the central catheter 312 is distended and the peripheral catheters 314 are exposed from beneath the sheath 394 and deployed. As shown in FIG. 11, the resilient devices 398 return to a thicker, less stretched condition and the adjacent portions of their associated peripheral catheters 314 bow outward away from the central catheter 312 when the peripheral catheters are retracted and covered by the sheath 394. To permit such outward bowing of the peripheral catheters 314, the passages 330 in the wall 316 of the central catheter 312 must be at least partially open to the outer surface 320 of the wall 316 adjacent the resilient devices 398. When the peripheral catheters 314 are withdrawn from the patient's tissue, the catheter assembly may be withdrawn from the cavity in the patient's tissue.

Although the peripheral catheters 314 are fixed, via the injection port assemblies 380, to the wall 316 of the central catheter 312, the peripheral catheters could be connected to the wall of the central catheter without being fixed to the wall. In particular, as the distal end portions 334 of the peripheral catheters 314 can be pulled away from the sheath 394 by the threads 390 in response to inflation of the central catheter 312, the proximal end portions 336 of the peripheral catheters 314 could be longitudinally movable relative to the central catheter. In such a catheter assembly, the injection port assemblies would not be fixed to the wall 316 of the central catheter 312, but rather would be movable along a portion of the length of the central catheter. The peripheral catheters 314 would remain connected to the wall 316 of the central catheter 312, however, via the threads 390 and via the radial constraint imposed by the surfaces of the wall 316 defining the passages 330 through which the peripheral catheters extend. In addition, in such a catheter, the resilient devices 398 could be positioned adjacent the proximal end portions 336 of the peripheral catheters 314 so as to pull the peripheral catheters resiliently in a direction along the length of the central catheter 312 without outward bowing as the central catheter deflates and the thinned end portion 326 returns to a non-distended or less distended condition.

As another alternative, the individual threads 390 could be combined into a single member, such a cap having a partially spherical shape. Such a cap would be positioned at and attached to the distal end 324 of the central catheter 312 and would, therefore, be diametrically opposite the sheath 394 when the thinned end portion 326 of the central catheter is distended. The junctions 392 between the peripheral catheters 314 and such a cap could be at the edge of the cap that surrounds its larger diameter open end or at the ends of partial threads extending from the edge of the cap that surrounds its larger diameter open end. As a further alternative, the threads 390 could be relatively short pieces of material.

The peripheral catheters 314, as well as the peripheral catheters 14, 114, and 214 of the embodiments of FIGS. 1-3, 4-5, and 6-9, respectively, may be made of a material having a shape memory. Such a shape memory material could be used to provide the peripheral catheters 14, 114, 214, and 314 with a substantially straight configuration at temperatures below a patient's normal body temperature. Such a shape memory material would provide the distal end portions 34, 134, 234, and 334 of the peripheral catheters 14, 114, 214, and 314 with a curved configuration when the peripheral catheters are exposed to a temperature at or above a patient's normal body temperature. Thus, when the catheter assemblies 10, 100, 200, and 300 using such a shape memory material were introduced into a patient's tissue, the patient's body temperature would cause the distal end portions 34, 134, 234, and 334 of the peripheral catheters 14, 114, 214, and 314 to assume a curved configuration and penetrate the patient's tissue.

As previously noted, each of the catheter assemblies 10, 100, 200, and 300 may have only single peripheral catheter 14, 114, 214, or 314 or may have an array of multiple peripheral catheters, such as six to eight or more. Moreover, although the distal end portions 34, 134, 234, and 334 of the peripheral catheters 14, 114, 214, and 314, respectively, are shown as having a predetermined curved configuration and as projecting radially outwardly from the central catheter 12, 112, 212, and 312, respectively, the distal end portions may have other predetermined configurations, such as a an angled or straight configuration, and may project from the central catheter in other directions, such as ninety degrees or another angle from the central catheter or axially through the distal end 24, 124, 224, and 324, respectively, of the central catheter. If the distal end portions 34 and 134 of the peripheral catheters 14 and 114, respectively, have a straight configuration and have no angle or curve with respect to the remaining portions of the peripheral catheters, the distal end portions will not be deflected by the walls 16 and 116 of the central catheters 12 and 112, respectively, when the walls are extended. Likewise, if the distal end portions 234 of the peripheral catheters 214 have a straight configuration and have no angle or curve with respect to the remaining portions of the peripheral catheters, the distal end portions 234 of the peripheral catheters will not be deflected by the sheaths 292 when the wall 216 of the central catheter 212 has not yet been distended or extended sufficiently to release the sheaths.

While the central catheters 12, 112, 212, and 312 and peripheral catheters 14, 114, 214, and 314 have been described as being introduced into a patient's tissue and then later removed from the patient's tissue, the central and/or peripheral catheters may be fabricated of a material or materials that can be absorbed by the tissue, thereby reducing or eliminating the requirement physically to remove the catheters from the patient's tissue. Further, the peripheral catheters 14, 114, 214, and 314 may be fabricated of an electrically conductive material and electrically insulated with a coating or jacket except at the tips of the distal end portions 34, 134, 234, and 334, respectively, of the peripheral catheters. The peripheral catheters 14, 114, 214, and 314 could thus function as electrodes, conducting electrical signals applied to the proximal end portions of the peripheral catheters to the patient's tissue for therapeutic electrical stimulation. Finally, while the use of biocompatible adhesive materials has been described above to secure the peripheral catheters 14, 114 to the wall 16, 116 of the central catheter 12, 112, as well as to secure or attach together other components of the catheter assemblies 10, 100, 200, and 300, other suitable attachment or fixation mechanisms, such as radio frequency welding and molded interlocking pins or other interlocking structural features, may be used where appropriate.

It will be appreciated that the catheter assemblies 10, 100, 200, and 300 may be used to treat both neoplastic and non-neoplastic disorders. Bioactive materials introduced into a patient's tissue using any of the catheter assemblies 10, 100, 200, and 300 may include, for example, chemotherapeutic materials, viruses, proteins, radiologic materials, growth factors, peptides, and non-radioactive tracer molecules. The catheter assemblies 10, 100, 200, and 300 may be used in a variety of patient tissues, including, for example, brain tissue, spinal cord tissue, and tissue of any organ.

From the above description of the invention, those skilled in the art will perceive improvements, changes and modifications. Such improvements, changes, and/or modifications within the skill of the art are intended to be covered by the appended claims.

Having described the invention, the following is claimed:

1. A catheter assembly comprising:
a first catheter including a wall with an inner surface at least partially defining a lumen, at least a portion of the wall of the first catheter being made of a resilient material and being resiliently extensible; and
a second catheter connected to the wall of the first catheter and disposed outward of the inner surface of the wall, the second catheter being at least partially covered by a sheath portion of the first catheter, resilient extension of said at least a portion of the wall of the first catheter causing at least a portion of the second catheter to assume one of a position covered by the sheath portion of the first catheter and a position projecting out the sheath portion of the first catheter.

2. A catheter assembly according to claim 1 wherein the sheath portion of the first catheter includes the wall of the first catheter, the wall having an outer surface, the second catheter being at least partially disposed between the inner and outer surfaces of the wall.

3. A catheter assembly according to claim 2 wherein the second catheter has a predetermined shape, the second catheter being deflected from the predetermined shape when disposed between the inner and outer surfaces of the wall of the first catheter.

4. A catheter assembly according to claim 3 wherein said at least a portion of the wall of the first catheter is a lengthwise portion of the wall of the first catheter, the lengthwise portion of the wall being longitudinally resiliently extensible, at least a portion of the second catheter being disposed between the inner and outer surfaces of the wall of the first catheter when the lengthwise portion of the wall is longitudinally extended, said at least a portion of the second catheter projecting out of the wall of the first catheter and assuming the predetermined shape when the lengthwise portion of the wall resiliently returns from a longitudinally extended condition.

5. A catheter assembly according to claim 4 wherein the lengthwise portion of the wall is a first lengthwise portion of the wall, the inner and outer surfaces of the wall of the first catheter being spaced apart (a) a first distance in the first lengthwise portion of the wall of the first catheter and (b) a second distance in a second lengthwise portion of the wall of the first catheter, the first distance being larger than the second distance.

6. A catheter assembly according to claim 1 wherein the wall of the first catheter has an outer surface, the sheath portion of the first catheter and at least a portion of the second catheter being disposed outward of the outer surface of the wall of the first catheter.

7. A catheter assembly according to claim 6 wherein the second catheter is at least partially fixed to the outer surface of the wall of the first catheter.

8. A catheter assembly according to claim 6 wherein the second catheter has a predetermined shape, the second catheter being deflected from the predetermined shape when covered by the sheath portion of the first catheter.

9. A catheter assembly according to claim 8 wherein the second catheter projects out of the sheath portion of the first catheter when said at least a portion of the wall is extended.

10. A catheter assembly according to claim 6 wherein the sheath portion of the first catheter is at least partially fixed to the wall of the first catheter.

11. A catheter assembly according to claim 6 wherein the sheath portion of the first catheter is at least partially releasably attached to the wall of the first catheter.

12. A catheter assembly according to claim 11 wherein the second catheter has a predetermined shape, the second catheter being deflected from the predetermined shape when covered by the sheath portion of the first catheter.

13. A catheter assembly according to claim 1 wherein the second catheter has a predetermined shape, the second catheter being deflected from the predetermined shape when covered by the sheath portion of the first catheter.

14. A catheter assembly according to claim 1 wherein the second catheter projects out of the sheath portion of the first catheter when said at least a portion of the wall is extended.

15. A catheter assembly according to claim 1 wherein resilient extension of said at least a portion of the wall causes a portion of the second catheter to be pulled in a direction away from the sheath portion of the first catheter and thereby uncovered.

16. A catheter assembly comprising:
a first catheter including a wall with an inner surface at least partially defining a first lumen, at least a portion of the wall of the first catheter being made of a resilient material and being longitudinally resiliently extensible; and
a second catheter including a second lumen, the second catheter being disposed outward of the inner surface of the wall of the first catheter, the second catheter being at least partially fixed to the wall of the first catheter, the first catheter being disposed outside of the second lumen, resilient extension of said at least a portion of the wall of the first catheter causing relative movement between said at least a portion of the wall and an adjacent portion of the second catheter.

17. A catheter assembly according to claim 16 wherein the wall of the first catheter has an outer surface, the second catheter being at least partially disposed between the inner and outer surfaces of the wall.

18. A catheter assembly according to claim 17 wherein the second catheter has a predetermined shape, the second catheter being deflected from the predetermined shape when disposed between the inner and outer surfaces of the wall of the first catheter.

19. A catheter assembly according to claim 18 wherein said at least a portion of the wall of the first catheter is a lengthwise portion of the wall of the first catheter, at least a portion of the second catheter being disposed between the inner and outer surfaces of the wall of the first catheter when the lengthwise portion of the wall is longitudinally extended, said at least a portion of the second catheter projecting out of the wall of the first catheter and assuming the predetermined shape when the lengthwise portion of the wall resiliently returns from a longitudinally extended condition.

20. A catheter assembly according to claim 19 wherein the lengthwise portion of the wall is a first lengthwise portion of the wall, the inner and outer surfaces of the wall of the first catheter being spaced apart (a) a first distance in the first lengthwise portion of the wall of the first catheter and (b) a second distance in a second lengthwise portion of the wall of the first catheter, the first distance being larger than the second distance.

21. A catheter assembly according to claim 16 wherein the wall of the first catheter has an outer surface, the second catheter being disposed outward of the outer surface of the wall of the first catheter, the second catheter being at least partially fixed to the outer surface of the first catheter.

22. A catheter assembly according to claim 21 wherein the second catheter is at least partially covered by a sheath portion of the first catheter.

23. A catheter assembly according to claim 22 wherein the second catheter has a predetermined shape, the second catheter being deflected from the predetermined shape when covered by the sheath portion of the first catheter.

24. A catheter assembly according to claim 22 wherein the second catheter projects out of the sheath portion of the first catheter when said at least a portion of the wall is extended.

25. A catheter assembly according to claim 22 wherein resilient extension of said at least a portion of the wall causes a portion of the second catheter to be pulled in a direction away from the sheath portion of the first catheter and thereby uncovered.

26. A catheter assembly comprising:
a first catheter including a wall with an inner surface at least partially defining a lumen extending lengthwise of the first catheter, at least a portion of the wall of the first catheter being made of a resilient material and being resiliently extensible; and
a second catheter at least partially disposed in the wall of the first catheter outward of the inner surface of the wall and extending lengthwise of the first catheter, resilient extension of said at least a portion of the wall of the first catheter causing relative movement between said at least a portion of the wall and an adjacent portion of the second catheter.

27. A catheter assembly according to claim 26 wherein the second catheter has a predetermined shape, the second catheter being deflected from the predetermined shape when disposed in the wall of the first catheter.

28. A catheter assembly according to claim 27 wherein at least a portion of the second catheter projects out of the wall of the first catheter and assumes the predetermined shape.

29. A catheter assembly according to claim 28 wherein said at least a portion of the second catheter is a distal portion of the second catheter and projects out of a distal portion of the wall of the first catheter.

30. A catheter assembly according to claim 29 wherein the second catheter also has an opposite proximal portion projecting out of a proximal portion of the wall of the first catheter, a fluid inlet port being in communication with the proximal portion of the second catheter.

31. A catheter assembly according to claim 29 wherein said at least a portion of the wall of the first catheter is a lengthwise portion of the wall of the first catheter, the distal portion of the second catheter being disposed between the inner and outer surfaces of the wall of the first catheter when the lengthwise portion of the wall is longitudinally resiliently extended, the distal portion of the second catheter projecting out of the wall of the first catheter and assuming the predetermined shape when the lengthwise portion of the wall resiliently returns from a longitudinally extended condition.

32. A catheter assembly according to claim 31 wherein the lengthwise portion of the wall is a first lengthwise portion of the wall, the inner and outer surfaces of the wall of the first catheter being spaced apart (a) a first distance in the first lengthwise portion of the wall of the first catheter and (b) a second distance in a second lengthwise portion of the wall of the first catheter, the first distance being larger than the second distance.

33. A catheter assembly according to claim 28 wherein said at least a portion of the second catheter is a distal portion of the second catheter and projects out of a distal portion of the wall of the first catheter, the second catheter also having an opposite end portion in fluid communication with the lumen of the first catheter.

34. A catheter assembly according to claim 33 wherein said at least a portion of the wall of the first catheter is a lengthwise portion of the wall of the first catheter, the lengthwise portion of the wall being longitudinally resiliently extensible, the distal portion of the second catheter being disposed between the inner and outer surfaces of the wall of the first catheter when the lengthwise portion of the wall is longitudinally resiliently extended, the distal portion of the second catheter projecting out of the wall of the first catheter and assuming the predetermined shape when the lengthwise portion of the wall resiliently returns from a longitudinally extended condition.

35. A catheter assembly according to claim 26 wherein said at least a portion of the wall of the first catheter is a lengthwise portion of the wall of the first catheter, the lengthwise portion of the wall being longitudinally resiliently extensible, the lengthwise portion of the wall of the first catheter having a diameter that is reduced when the lengthwise portion of the wall is longitudinally resiliently extended, the diameter of the lengthwise portion of the wall increasing from a reduced condition when the lengthwise portion of the wall resiliently returns from a longitudinally extended condition.

36. A catheter assembly according to claim 26 wherein the second catheter is at least partially covered by a sheath portion of the first catheter, resilient extension of said at least a portion of the wall causing a portion of the second catheter to be pulled in a direction away from the sheath portion of the first catheter and thereby uncovered.

37. A catheter assembly comprising a catheter having a wall at least partially defining a lumen, the wall of the catheter having an inner surface and an outer surface, a first lengthwise portion of the wall being made of a resilient material and being longitudinally resiliently extensible, the first lengthwise portion of the wall having a diameter that is reduced when the first lengthwise portion of the wall is longitudinally resiliently extended, the diameter of the first lengthwise portion of the wall increasing from a reduced condition when the first lengthwise portion of the wall resiliently returns from a longitudinally extended condition, the inner and outer surfaces of the wall of the first catheter being spaced apart (a) a first distance along a length of the first lengthwise portion of the wall of the catheter and (b) a second distance along a length of a second lengthwise portion of the wall of the catheter, the first distance being larger than the second distance.

38. A catheter assembly comprising:
a first catheter including a wall with an inner surface at least partially defining a lumen; and
a second catheter disposed outward of the inner surface of the wall,
at least a portion of the wall of the first catheter being made of a resilient material and being resiliently extensible, the second catheter being connected to said at least a portion of the wall of the first catheter, resilient extension of said at least a portion of the wall causing a portion of the second catheter to be pulled from a first position to a second position.

39. A catheter assembly according to claim 38 further comprising a piece of material that is less extensible than said at least a portion of the wall of the first catheter, the piece of material being connected to the second catheter and to said at least a portion of the wall of the first catheter, resilient extension of said at least a portion of the wall causing the piece of material to pull the portion of the second catheter from the first position to the second position.

40. A catheter assembly according to claim 38 wherein said at least a portion of the wall of the first catheter constitutes a balloon portion of the first catheter.

41. A catheter assembly comprising:
a first catheter including a first lumen;
a second catheter; and
a piece of material connected to the first catheter,
movement of the second catheter causing the piece of material to move and pull at least a portion of the first catheter from a first position to a second position.

42. A catheter assembly according to claim 41 wherein the second catheter includes a wall with an inner surface at least partially defining a second lumen, at least a portion of the wall being made of a resilient material and being resiliently extensible, the piece of material being disposed outside of the first lumen and outward of the inner surface of the wall of the second catheter, the piece of material being elongated and connecting the first catheter to said at least a portion of the wall of the second catheter, resilient extension of said at least a portion of the wall causing the piece of material to move and pull the portion of the first catheter from the first position to the second position.

43. A catheter assembly comprising:
a first catheter including a wall with an inner surface at least partially defining a lumen, at least a portion of the wall of the first catheter being made of a resilient material and being extensible; and
a second catheter connected to the wall of the first catheter and disposed outward of the inner surface of the wall, the second catheter being at least partially covered by a sheath portion of the first catheter,
the wall of the first catheter having an outer surface, the sheath portion of the first catheter and at least a portion of the second catheter being disposed outward of the outer surface of the wall of the first catheter, the sheath portion of the first catheter is at least partially releasably attached to the wall of the first catheter.

44. A catheter assembly according to claim 43 wherein the second catheter has a predetermined shape, the second catheter being deflected from the predetermined shape when covered by the sheath portion of the first catheter.

* * * * *